United States Patent [19]

Matsuno et al.

[11] Patent Number: 4,985,237
[45] Date of Patent: Jan. 15, 1991

[54] BENZYLIDENE COMPOUNDS, COSMETIC COMPOSITIONS CONTAINING THE SAME AND ULTRAVIOLET ABSORBER COMPRISING THE SAME

[75] Inventors: Kazuhiro Matsuno; Toru Kobayashi; Takeshi Miyoshi; Hideaki Kawashima, all of Kawasaki, Japan

[73] Assignee: Ajinomoto Co., Inc., Tokyo, Japan

[21] Appl. No.: 259,257

[22] Filed: Oct. 18, 1988

Related U.S. Application Data

[62] Division of Ser. No. 38,364, Apr. 14, 1987, Pat. No. 4,797,493.

[30] Foreign Application Priority Data

Apr. 22, 1986 [JP] Japan .................... 61-92481
Oct. 16, 1986 [JP] Japan .................... 61-246308
Oct. 16, 1986 [JP] Japan .................... 61-246309
Nov. 14, 1986 [JP] Japan .................... 61-271287

[51] Int. Cl.$^5$ .............. A61K 7/021; A61K 7/42; A61K 9/10; A61K 9/12
[52] U.S. Cl. .................... 424/59; 424/DIG. 5; 424/47; 424/60; 424/63; 424/64; 424/69; 424/70; 424/71; 424/78; 514/845; 514/847; 514/873; 514/937; 514/938; 514/944; 514/969
[58] Field of Search .................... 424/59, 60

[56] References Cited

U.S. PATENT DOCUMENTS 3,365,296 1/1968 Cox et al. .................... 424/59
4,797,493 1/1989 Matsuno et al. .................... 548/312

FOREIGN PATENT DOCUMENTS 0198397 10/1986 European Pat. Off. .................... 424/59
2375867 7/1978 France .................... 424/59
2083240 3/1982 United Kingdom .................... 424/59

OTHER PUBLICATIONS

Chemical Abstract, vol. 88, No. 3, Jan. 1978, Abstract No. 22747T.
Chemical Abstract, vol. 104, No. 7, Feb. 1986, Abstract No. 50807E.
Chemical Abstracts Service Registry Handbook, 1986, p. 963RO.

*Primary Examiner*—Dale R. Ore
*Attorney, Agent, or Firm*—Oblon, Spivak, McClelland, Maier & Neustadt

[57] ABSTRACT

Disclosed herein are benzylidene compounds represented by the formula (I):

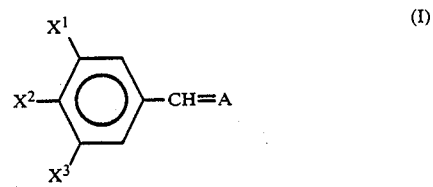

wherein A represents

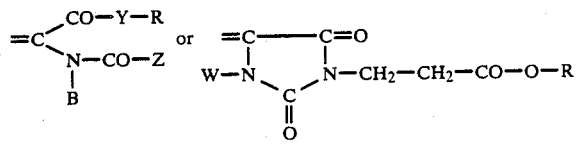

(wherein B represents hydrogen atom or an acetyl group, W represents hydrogen atom or $-CH_2-CH_2-CO-O-R$, $X^1$, $X^2$ and $X^3$ represent independently hydrogen atom, a hydroxyl group or a methoxyl group (two or three of them may be the same or all of them may be different), Y represents oxygen atom or imino group ($-NH-$), Z represents a methyl group or a phenyl group, and R represents a straight chain alkyl group having 1 to 18 carbon atoms, or branched or cyclic alkyl group having 3 to 18 carbon atoms, provided that when A is (Abstract continued on next page.)

R is not an alkyl group having 1 to 2 carbon atoms, and
when A is
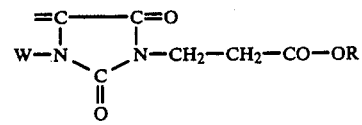
and $X^1$, $X^2$ and $X^3$ are hydrogen atom, R is not an alkyl group having 1 to 2 carbon atoms), a cosmetic composition containing the same and an ultraviolet absorber comprising the same.
10 Claims, 19 Drawing Sheets

BENZYLIDENE COMPOUNDS, COSMETIC COMPOSITIONS CONTAINING THE SAME AND ULTRAVIOLET ABSORBER COMPRISING THE SAME

This is a division, of application Ser. No 07/038,364, filed Apr. 14, 1987, now U.S. Pat. No. 4,797,493.

BACKGROUND OF THE INVENTION

The present invention relates to the novel benzylidene compounds, an ultraviolet-absorbing cosmetic composition and an ultraviolet absorber. More particularly, the invention relates to benzylidene compounds represented by the formula (1):

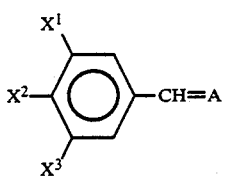

wherein A is a group represented by the formula (II):

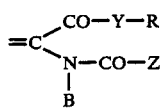

or the formula (III)

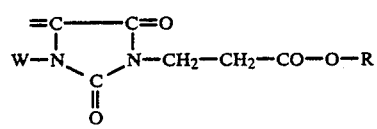

wherein B represents hydrogen atom or an acetyl group; W represents hydrogen atom or $-CH_2-CH_2-CO-O-R$; $X^1$, $X^2$ and $X^3$ represent independently hydrogen atom, a hydroxyl group or a methoxyl group (two or three of $X^1$, $X^2$ and $X^3$ may be the same or all of them may be different); Y represents oxygen atom or an imino group ($-NH-$); Z represents a methyl group or a phenyl group; and R represents a straight chain alkyl group having 1 to 18 carbon atoms, or branched or cyclic alkyl group having 3 to 18 carbon atoms, provided that when A is a group represented by the formula (II), R is not an alkyl group having 1 to 2 carbon atoms, and when A is a group represented by the formula (111) and $X^1$, $X^2$ and $X^3$ are hydrogen atom, R is not an alkyl group having 1 to 2 carbon atoms, an ultraviolet-absorbing cosmetic composition containing at least one of the benzylidene compounds represented by the formula (1), and an ultraviolet absorber comprising at least one of the benzylidene compounds represented by the formula (1).

In the field of cosmetics, use of ultraviolet absorbers has been noted from long age for preventing the harmful effect of ultraviolet rays to the skin and a number of ultraviolet absorbers for use in cosmetics have been developed.

It is known that ultraviolet rays, when the skin has been exposed thereto, cause various changes in the skin tissue. In the dermatology, ultraviolet rays are classified into long-wavelength ultraviolet rays (400–320 nm), medium-wavelength ultraviolet rays (320–290 nm) and short-wavelength ultraviolet rays (290–100 nm), and they are referred to as UV-A, UV-B and UV—C, respectively.

Among them, UV—C is absorbed in the ozone layer and scarcely reaches the surface of the earth. As for UV-B, it is known that when the skin is exposed to UV-B at a dose of more than a certain level, UV-B causes erythema or blisters on the skin or causes pigmentation in the skin. On the other hand, UV-A has been said to exert no much influence on the skin. However, as a result of examinations by electron microscopes and histological investigations, it was found recently that UV-A does cause a change in elastic fibers in vascular walls or connective tissues. Further, UV-A gives a damage to the hypersensitive skin or the skin exposed to the sunlight for a long time. It has been also reported that UV-A promotes the action of UV-B (J. Willis, A. Kligman and J. Epstein: "Photo-enhancement", The Journal of Investigative Dermatology, Vol. 59, No. 6, p. 416, 1973). Thus, screening the skin from UV-A is as important as that from UV-B.

As UV-B absorbers, there are used benzophenones. absorbers, salicylic acids absorbers, cinnamic acids absorbers, para-aminobenzoic acids absorbers, etc. Among such known ultraviolet absorbers, however, there are few which are satisfactory in effect, safety, solubility, stability and other properties The history of study on UV-A is not long, and materials which, when applied to the skin, can effectively absorb UV-A are scarcely known. Only such materials known are dibenzoylmethane derivatives, cinnamic acid derivatives and chalcone derivatives [West German Patent Application Laid-Open Nos. 2,728,241 and 2,728,243, and Japanese Patent Application Laid-Open (KOKAI) Nos. 51-61641('76), 52-46056('77), 57-59840('82), 57-19720('82) and 60-109544('85)].

For instance, Japanese Patent Application Laid-Open (KOKAI) No. 51-61641('76) discloses a light screening agent containing a compound of the formula:

(wherein R is an alkyl group having 1 to 3 carbon atoms) with a miscible cosmetic base, and Japanese Patent Application Laid-Open (KOKAI) No. 52-46056('77) discloses an ultraviolet absorber containing at least one of the compounds represented by the formula:

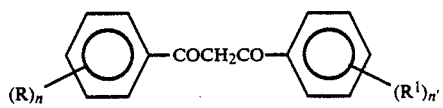

(wherein R and $R^1$ represent a straight chain or branched alkyl group having 1 to 8 carbon atoms, n is an integer of 0 to 3, and n' is an integer of 1 to 3). Japanese Patent Application Laid-Open (KOKAI) No. 57-59840('82) discloses a composition having the properties for protecting the skin from ultraviolet radiation, which comprises at least one of the dibenzoylmethane derivatives represented by the formula:

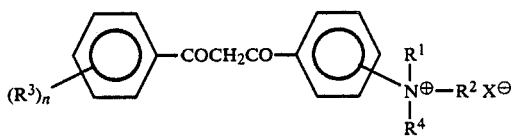

(wherein R¹ and R² represent a lower alkyl group or a hydroxyalkyl group, R³ represents a lower alkyl group or an alkoxyl group, n is an integer of 0 to 3, and X⊖ represents anion derived from a mineral acid or an organic acid) and a cosmetically acceptable carrier. Japanese Patent Application Laid-Open (KOKAI) No. 57-197209('82) discloses a composition comprising as a light screening agent at least one of the hydroxyl derivatives of dibenzoylmethanes of the formula:

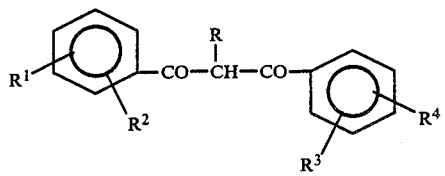

(wherein R¹, R², R³ and R⁴ represent hydrogen atom, a halogen atom, a straight chain or branched alkyl group having 1 to 12 carbon atoms, or an alkoxyl group having 1 to 4 carbon atoms, and R represents hydrogen atom or an alkyl group having 1 to 4 carbon atoms) and a cosmetically acceptable carrier. Also, Japanese Patent Application Laid-Open (KOKAI) No. 60-109544('85) discloses an ultraviolet absorber containing as an active ingredient a chalcone derivative represented by the formula:

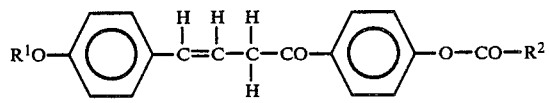

(wherein R¹ represents hydrogen atom or a methyl group, and R² represents a straight chain or branched aliphatic hydrocarbon group having 2 to 24 carbon atoms).

Besides the above-mentioned ultraviolet absorbers, there are also used the inorganic powders having the function to physically reflect or scatter the ultraviolet rays, such as titanium dioxide, zinc oxide, iron oxide, etc.

The benzophenones ultraviolet absorbers have an activity of absorbing long-wavelength ultraviolet rays (320-400 nm) but are low in absorptivity of medium-wavelength ultraviolet rays (290-320 nm) which are considered to cause blistering, etc., of the skin.

The para-aminobenzoic acids and cinnamic acids ultraviolet absorbers are high in UV absorbing effect, but it is said that they have the problem in stability. The salicylic acids Uv absorbers are low in UV absorbing effect, so that no satisfactory effect can be expected unless they are blended in a large amount.

The inorganic powders are limited in their use to certain cosmetics types in which they can be compounded, and they also have the problem that they might be colored when compounded in a large quantity.

Ultraviolet absorbers are also used as an additive for preventing deterioration of resins. As an additive, salicylic acids UV absorbers, benzophenones UV absorbers, triazoles UV absorbers and cyanoacrylates UV absorbers are exemplified However, the salicylic acids and benzophenones UV absorbers are low in absorptivity of ultraviolet rays of wavelength of around 300-320 nm which are said to give influences to resins such as polyethylene, polypropylene and polyvinyl chloride, while the triazoles UV absorbers are said to have the problem in safety and sanitation.

As described above, although various ultraviolet absorbers have been developed, there is yet available no ultraviolet absorber which can meet all of the requirements for UV absorptivity, safety, solubility in solvents and resins, and stability. Thus, the realization of an ultraviolet absorber having excellent UV absorptivity, safety and stability and a cosmetic composition containing such UV absorber has been desired.

In view of the above, as a result of more extensive studies, it has been found that the benzylidene compounds represented by the general formula (I) have a high absorptivity of ultraviolet rays of medium wavelength (240-400 nm) and are also easily soluble in various kinds of animal oils, vegetable oils, fats and oils, and organic solvents, and that the cosmetic compositions containing at least one of such compounds are possessed of good UV absorptivity, effective for preventing erythema, etc., of the skin, stable to light and heat, and also not stimulant nor injurious to the skin, lips, hair, nails, etc. The present invention has been attained on the basis of such finding.

SUMMARY OF THE INVENTION:

In a first aspect of the present invention, there is provided benzylidene compounds represented by the formula (1):

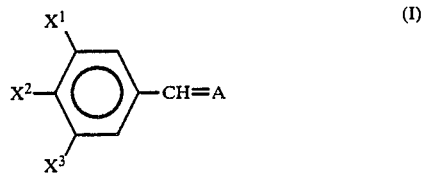 (I)

wherein A represents

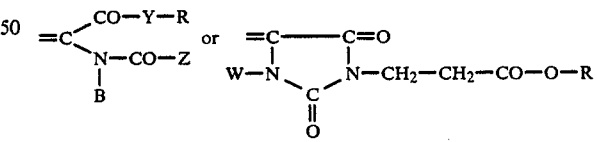

(wherein B represents hydrogen atom or an acetyl group, W represents hydrogen atom or —CH₂—CH₂—CO—O—R, X¹, X² and X³ represent independently hydrogen atom, a hydroxyl group or a methoxyl group (two or three of then may be the same or all of them may be different), Y represents oxygen atom or imino group (—NH—), Z represents a methyl group or a phenyl group, and R represents a straight chain alkyl group having 1 to 18 carbon atoms, or branched or cyclic alkyl group having 3 to 18 carbon atoms, provided that when A is

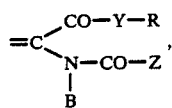

R is not an alkyl group having 1 to 2 carbon atoms, and when A is

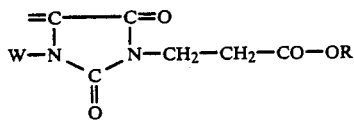

and $X^1$, $X^2$ and $X^3$ are hydrogen atom, R is not an alkyl group having 1 to 2 carbon atoms).

In a second aspect of the present invention, there is provided a cosmetic composition containing at least one of compounds of the formula (I):

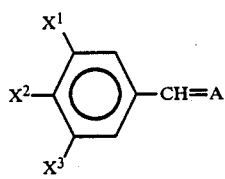

(I)

wherein A represents

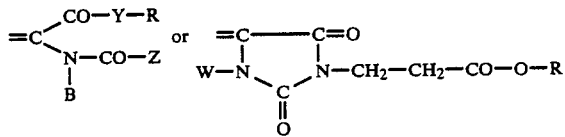

(wherein B represents hydrogen atom or an acetyl group, W represents hydrogen atom or —CH$_2$—CH$_2$—CO—O—R, $X^1$, $X^2$ and $X^3$ represent independently hydrogen atom, a hydroxyl group or a methoxyl group (two or three of them may be the same or all of them may be different), Y represents oxygen atom or an imino group (—NH—), Z represents a methyl group or a phenyl group, and R represents a straight chain alkyl group having 1 to 18 carbon atoms, or branched or cyclic alkyl group having 3 to 18 carbon atoms, provided that when A is

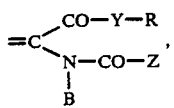

R is not an alkyl group having 1 to 2 carbon atoms, and when A is

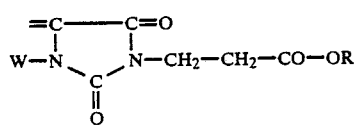

and $X^1$, $X^2$ and $X^3$ are hydrogen atom, R is not an alkyl group having 1 to 2 carbon atoms).

In a third aspect of the present invention, there is provided an ultraviolet absorber comprising at least one of the compounds of the formula (I):

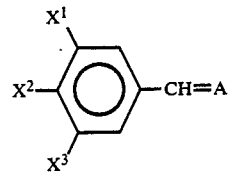

(I)

wherein A represents

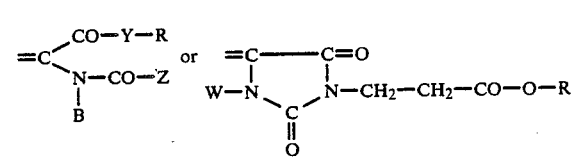

(wherein B represents hydrogen atom or an acetyl group, W represents hydrogen atom or —CH$_2$—CH$_2$—CO—O—R, $X^1$, $X^2$ and $X^3$ represent independently hydrogen atom, a hydroxyl group or a methoxyl group (two or three of them may be the same or all of them may be different), Y represents oxygen atom or an imino group (—NH—), Z represents a methyl group or a phenyl group, and R represents a straight chain alkyl group having 1 to 18 carbon atoms, or branched or cyclic alkyl group having 3 to 18 carbon atoms, provided that when A is

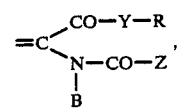

R is not an alkyl group having 1 to 2 carbon atoms, and when A is

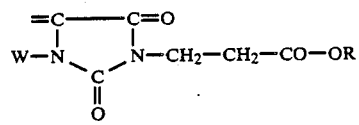

and $X^1$, $X^2$ and $X^3$ are hydrogen atom, R is not an alkyl group having 1 to 2 carbon atoms).

DETAILED DESCRIPTION OF THE INVENTION

Figure 1:
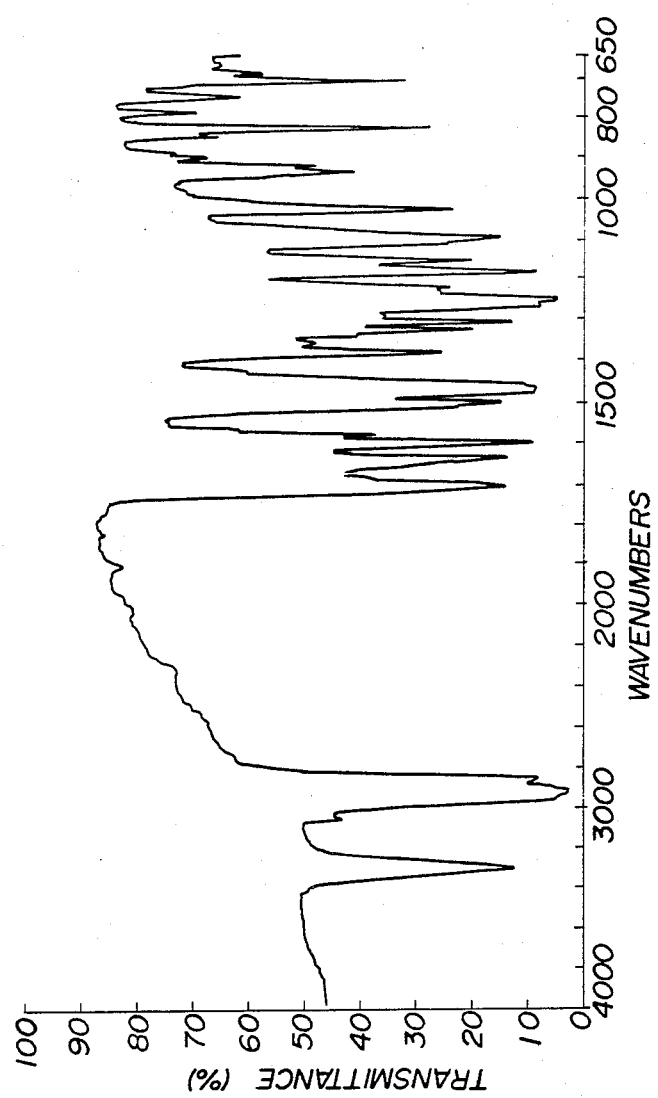
FIGS. 1 to 19 show the respective infrared absorption spectra of compounds Nos. 1 to 19 according to the present invention.

The compounds of the formula (1) according to the present invention can be classified roughly into compounds of the formula (I) in which A is a group of the formula (II), namely the compounds represented by the following formula (IV):

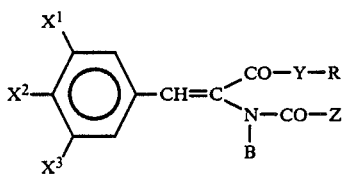
(IV)

(wherein B is hydrogen atom or an acetyl group, each of $X^1$, $X^2$ and $X^3$ are hydrogen atom, a hydroxyl group or a methoxyl group, Y is oxygen atom or an imino group (—NH—), Z is a methyl group or a phenyl group, and R is a straight chain, branched or cyclic alkyl group having 3 to 18 carbon atoms, and compounds of the formula (1) in which A is a group of the formula (III), namely the compounds represented by the following formula (V):

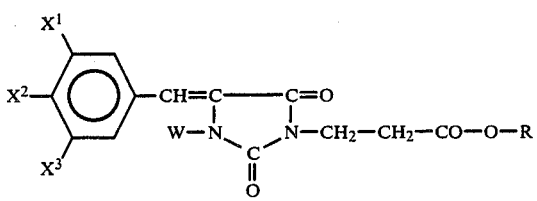
(V)

wherein (1) $X^1$ and $X^3$ are hydrogen atom or a methoxyl group, $X^2$ is a methoxyl group or a hydroxyl group, W is hydrogen atom or —CH$_2$—CH$_2$—COOR, and R is a straight chain alkyl group having 1 to 18 carbon atoms, or branched or cyclic alkyl group having 3 to 18 carbon atoms, or (2) $X^1$, $X^2$ and $X^3$ are hydrogen atom, W is hydrogen atom or —CH$_2$—CH$_2$—COOR, and R is a straight chain, branched or cyclic alkyl group having 3 to 18 carbon atoms, in which all of them are the novel compounds.

Preferable compounds of the present invention are: the compounds represented by the formula (IV) wherein B is hydrogen atom or an acetyl group, $X^1$ and $X^3$ are hydrogen atom or a methoxyl group, $X^2$ is a methoxyl group or a hydroxyl group, Y is oxygen atom or an imino group and R is an isopropyl group, an n-butyl group, an isobutyl group, an amyl group, an iso-amyl group, an n-hexyl group, a cyclohexyl group, an n-octyl group, a 2-ethylhexyl group, a 2,2,4-trimethylcyclohexyl group, a decyl group, a lauryl group, a myristyl group, a cetyl group or a stearyl group, the compounds represented by the formula (V) wherein $X^1$ and $X^2$ are a methoxyl group, $X^3$ is hydrogen atom, W is hydrogen atom or —CH$_2$—CH$_2$—CO—O—R and R is a methyl group, an ethyl group, an isopropyl group, an n-butyl group, an isobutyl group, an amyl group, an isoamyl group, an n-hexyl group, a cyclohexyl group, an n-octyl group, a 2-ethylhexyl group, a 2,2,4-trimethylcyclohexyl group, a decyl group, a lauryl group, a myristyl group, a cetyl group or a stearyl group, and the compounds represented by the formula (V) wherein $X^1$, $X^2$ and $X^3$ are hydrogen atom, W is hydrogen atom or —CH$_2$—CH$_2$CO—O—R and R is an isopropyl group, an n-butyl group, an isobutyl group, an amyl group, an isoamyl group, an n-hexyl group, a cyclohexyl group, an n-octyl group, a 2-ethylhexyl group, a 2,2,4-trimethylcyclohexyl group, a decyl group, a lauryl group, a myristyl group, a cetyl group or a stearyl group.

More preferable compounds of the present invention are:

the compounds represented by the formula (IV) wherein B is hydrogen atom or an acetyl group, $X^1$ and $X^3$ are or hydrogen atom, $X^2$ is a methoxyl group, Y is oxygen atom or an imino group (—NH—), Z is a methyl group or a phenyl group, and R is an isopropyl, 2-ethylhexyl, lauryl, isostearyl, cyclohexyl or 3,3,5-trimethylcyclohexyl group, the compounds represented by the formula (V) wherein $X^1$ and $X^2$ are a methoxyl group, $X^3$ is hydrogen atom, W is hydrogen atom or —CH$_2$CH$_2$COOR, and R is a methyl, ethyl, n-butyl, isobutyl or 2-ethylhexyl group, and l the compounds represented by the formula (V) wherein $X^1$, $X^2$ and $X^3$ are hydrogen atom, W is hydrogen atom, and R is an n-butyl, isobutyl or 2-ethylhexyl group. I The compounds represented by the formula (IV) can be prepared by the following processes:

(1) An aromatic aldehyde of the formula (VI) shown below and (i-1) an acetylglycine or benzoylglycine of the formula (VII) shown below or (i-2) an azlactone precursor of the formula (IX) shown below are condensed in the presence of a basic catalyst, and (ii-1) the produced alactone compound represented by the formula (VIII) shown below is hydrolyzed and then esterified or subjected to an amidation, or (ii-2) the produced alactone compound represented by the formula (VIII) shown below is directly subjected to alcoholysis or aminolysis, and (iii) if necessary the nitrogen atoms of the amide are acetylated.

(2) An α-keto-acid or an ester of the formula (X) shown below and an imine or amide of phosphine of the formula (XI) shown below are condensed. (3) An N-hydroxyamino ester of the formula (XII) shown below and a compound of the formula (XIII) shown below are reacted, and the resulting N-hydroxylamino acid ester of the formals (XIV) shown below is dehydrated.

The reaction formulae in the above-described preparation processes (1) - (3) are as follows:

Process (1)

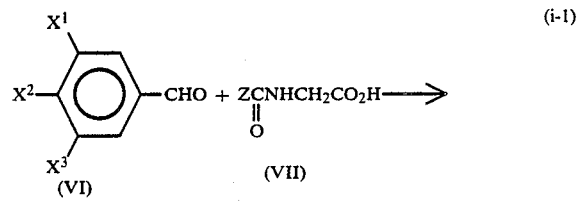
(i-1)

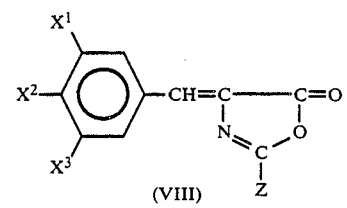
(VIII)

or

Process (2)

(i-2)

$$\text{(VI)} + \text{(IX)} \longrightarrow \text{(VIII)}$$

Ar-CHO + H$_2$O-C(=O)-O-C(Z)=N → (VIII)

(VIII): Ar-CH=C(-C(=O)-O-)N=C-Z (azlactone with benzylidene)

(ii-1) Hydrolysis of (VIII):

(VIII) $\xrightarrow{\text{Hydrolysis}}$ Ar-CH=C(COOH)(NHCZ=O)

$\xrightarrow{\text{esterification or amidation}}$ Ar-CH=C(COYR)(NHCZ=O)  (IV')

(ii-2) Alcoholysis or aminolysis:

(VIII) $\xrightarrow{\text{alcoholysis or aminolysis}}$ (IV')

(iii) When acylation is further conducted:

Compound of formula (I') [compound of formula (IV) where B = H] $\xrightarrow{\text{CH}_3\text{COCl}}$ Ar-CH=C(COYR)(N(CZ=O)(COCH$_3$))  (IV'')

(wherein $X^1$, $X^2$, $X^3$, Y, Z and R are as defined above).

Process (2)

$$\text{Ar-CH}_2\text{-CO-CO-Y-R} \quad (X)$$

$$(C_6H_5)_3P=N-C(=O)-Z \quad (XI)$$

$(X) + (XI) \longrightarrow$ Ar-CH=C(COYR)(NHCZ=O)  (IV')

(wherein $X^1$, $X^2$, $X^3$, Y, Z and R are as defined above).

Process (3)

Ar-CH$_2$-CH(NHOH)-CO-R  (XII) + ZCOCl  (XIII) →

Ar-CH$_2$-CH(N(OH)CZ=O)-CO-R  (XIV) $\xrightarrow{\text{Dehydration}}$

Ar-CH=C(COYR)(NHCZ=O)  (IV')

(wherein $X^1$, $X^2$, $X^3$, Y, Z and R are as defined above).

The condensation reaction of an aromatic aldehyde of the formula (VI) and an acetylglycine of benzoylglycine of the formula (VII) in the presence of a basic catalyst in the process (1) is carried out at a temperature of ) 0° to 150° C.

The condensation reaction of an aromatic aldehyde of the formula (VI) and an azlactone precursor of the formula (IX) in the presence of a basic catalyst is carried out at a temperature of 70° to 150° C. As the basic catalyst, there can be used an amine such as piperidine and triethyl amine, a metal alcoholate such as sodium alcoholate, potassium alcoholate, etc., sodium acetate, butyl lithium, sodium hydroxide, potassium hydroxide and the like.

The hydrolysis of the produced azlactone compound represented by the formula (VIII) is carried out at a temperature of 10° to 150° C. The esterification or amidation of the hydrolysed compound is carried out at a temperature of 0° to 150° C.

The alcoholysis of azlactone compound represented by the formula (VIII) is preferably carried out by using a basic catalyst such as a metal alcoholate (i.e. sodium alcoholate, potassium alcoholate, etc.), sodium hydroxide, potassium hydroxide, etc., at a temperature of 10 to 150° C. The acetylation of the nitrogen atoms of the amide in the compound of the formula (I') is preferably carried out by using a catalyst such as dimethylaminopyridine, pyrolidinopyridine, etc., at a temperature of −30° to 150° C.

The condensation reaction of an α-keto-acid or an ester of the formula (X) and an imine or amine of phosphine of the formula (XI) in the process (2) is carried out at a temperature of −30° to 150° C.

The reaction of an N-hydroxyamino ester compound of the formula (XII) and a compound of the formula (XIII) in the process (3) is carried out in the presence of a catalyst such as pyridine, dimethylaminopyridine and pyrolidinopyridine at a temperature of −30° to 150° C. The dehydration reaction of the N-hydroxyamino acid ester compound of the formula (XIV) is carried out at a temperature of 50° to 250° C. II. The compounds represented by the formula (V) can be prepared by a process which comprises:

'An aromatic aldehyde of the formula (VI) and a hydantoin of the formula (XV) are condensed in the presence of a basic catalyst, and an acrylic ester of the formula (XVII) is subjected to Michael addition to the produced benzalhydantoin of the formula (XVI).

The reaction formulae in this preparation process are as shown below:

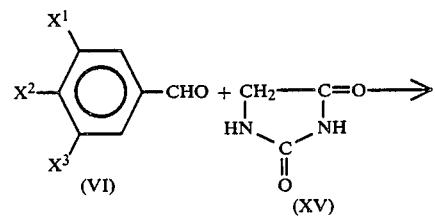

(i)

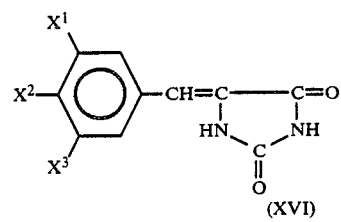

(XVI)

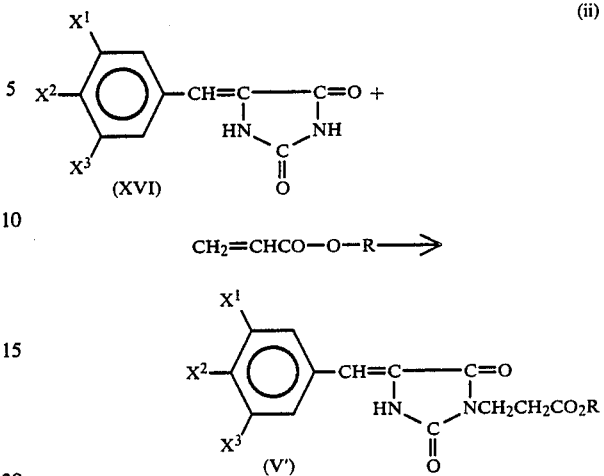

(wherein $X^1$, $X^2$, $X^3$ and R are as defined above).

The condensation reaction of an aromatic aldehyde of the formula (VI) and a hydantoin of the formula (XV) is carried out at a temperature of 0° to 150° C.

As the basic catalyst, there can be used an amine such as piperidine, triethyl amine, amino acid, aqueous ammonia, a metal alcoholate such as sodium alcoholate, potassium alcoholate, etc., sodium acetate, sodium hydroxide, potassium hydroxide, and the like.

The reaction for Michael addition of an acrylic ester of the formula (XVII) to the benzalhydantoin of the formula (XVI) is carried out at a temperature of 20° to 200° C.

Shown below are the examples of the compounds of the formula (IV) according to the present invention:

N-benzoyl-O-methyl-α-dehydrotyrosine laurylamide, N-benzoyl-O-methyl-α-dehydrotyrosine isopropyl ester, N-benzoyl-O-methyl-α-dehydrotyrosine lauryl ester, N-benzoyl-O-methyl-α-dehydrotyrosine stearyl ester, N-benzoyl-O-methyl-α-dehydrotyrosine 2-ethylhexyl ester, N-benzoyl-O-methyl-α-dehydrotyrosine cyclohexyl ester, N-benzoyl-O-methyl-α-dehydrotyrosine 3,3,5-trimethylcyclohexyl ester, N-acetyl-O-methyl-α-dehydrotyrosine isopropyl ester, N-acetyl-O-methyl-α-dehydrotyrosine 2-ethylhexyl ester, N-acetyl-O-methyl-α-dehydrotyrosine lauryl ester, N-acetyl-O-methyl-α-dehydrotyrosine stearyl ester, N-acetyl-N-benzoyl-O-methyl-α-dehydrotyrosine isopropyl ester, N-acetyl-N-benzoyl-O-methyl-α-dehydrotyrosine 2-ethylhexyl ester, N-acetyl-N-benzoyl-O-methyl-α-dehydrotyrosine lauryl ester, N-acetyl-N-benzoyl-O-methyl-α-dehydrotyrosine stearyl ester, N,N-diacetyl-O-methyl-α-dehydrotyrosine isopropyl ester, N,N-diacetyl-O-methyl-α-dehydrotyrosine 2-ethylhexyl ester, N,N-diacetyl-O-methyl-α-dehydrotyrosine lauryl ester, N,N-diacetyl-O-methyl-α-dehydrotyrosine stearyl ester, N-acetyl-N-benzoyl-O-methyl-α-dehydrotyrosine n-butyl ester, N,N-diacetyl-O-methyl-α-dehydrotyrosine n-butyl ester, and N-benzoyl-3,4,5-trimethoxy-α-dehydrophenylalanine 2-ethylhexyl ester.

Examples of the compounds of the formula (V) according to this invention are:

diisopropyl 4-benzylidene-2,5-dioxo-1,3-imidazolidinedipropionate, di-n-butyl 4-benzylidene-2,5-dioxo-1,3-imidazolidinedipropionate, diisobutyl 4-benzylidene-2,5-dioxo-1,3-imidazolidinedipropionate, bis(2-ethylhexyl) 4-benzylidene-2,5-dioxo-1,3-imidazolydinedipropionate, isopropyl 4-benzylidene-2,5-dioxo-1-imidazolidinepropionate, n-butyl 4-benzylidene-2,5-dioxo-1-imidazolidinepropionate, isobutyl 4-benzylidene-2,5-dioxo-1-imidazolidinepropionate, 2-ethylhexyl 4-benzylidene-2,5-dioxo-1-imidazolidinepropionate, dimethyl 4-(3,4-dimethoxyphenyl)methylene-2,5-dioxo-1,3-imidazolidinedipropionate, diethyl 4-(3,4-dimethoxyphenyl)-methylene-2,5-dioxo-1,3-imidazolidinedipropionate, diisopropyl 4-(3,4-dimethoxyphenyl)methylene-2,5-dioxo-1,3-imidazolidinedipropionate, di-n-butyl 4-(3,4-dimethoxyphenyl)-methylene-2,5-dioxo-1,3-imidazolidinedipropionate, diisobutyl 4-(3,4-dimethoxyphenyl)methylene-2,5-dioxo-1,3-imidazolidinedipropionate, bis(2-ethylhexyl)4-(3,4-dimethoxyphenyl)methylene-2,5-dioxo-1,3-imidazolidinedipropionate, isopropyl 4-(3,4-dimethoxyphenyl)-methylene-2,5-dioxo-1-imidazolidinepropionate, methyl 4-(3,4-dimethoxyphenyl)methylene-2,5-dioxo-1-imidazolidinepropionate, ethyl 4-(3,4-dimethoxyphenyl)methylene-2,5-dioxo-1-imidazolidinepropionate, n-butyl 4-(3,4-dimethoxyphenyl)methylene-2,5-dioxo-1-imidazolidinepropionate, isobutyl 4-(3,4-dimethoxyphenyl)methylene-2,5-dioxo-1-imidazolidinepropionate, 2-ethylhexyl 4-(3,4-dimethoxyphenyl)methylene-2,5-dioxo-1-imidazolidinepropionate, ethyl 4-(4-methoxyphenyl)methylene- 2,5-dioxo-1-imidazolidinepropionate, and ethyl 4-(3,4,5-trimethoxyphenyl)methylene-2,5-dioxo-1-imidazolidinepropionate.

The cosmetic compositions according to the present invention are composed of the compounds represented by the general formula (I) and the known components generally used in the cosmetic compositions, that is, an oil phase component, an aqueous phase component, a powder component and/or a surfactant component for emulsifying, dispersing or solubilizing these component materials.

Examples of the known components usable in the composition of the present invention are shown below. As an oil phase component, animal and vegetable oils such as beeswax, Japan wax, whale wax, carnauba wax, candelilla wax, cacao oil, cetyl alcohol, stearyl alcohol, oleic acid, stearic acid, lanoline, olive oil, tsubaki oil, cottonseed oil, castor oil, oleyl alcohol, squalane, etc.; mineral oils and fats such as solid paraffin, ceresine, microcrystalline wax, vaseline, liquid paraffin, silicone oil, etc.; and synthetic oils and fats such as isopropyl myristate, synthetic polyether, etc. may be exemplified. As an aqueous phase component, glycerin, propylene glycol, sorbitol, polyethylene glycol, Quine Seed gum, Tragacanth gum, alginates, pectin, carboxymethyl cellulose, hyaluronic acid, water-soluble chitin, polyvinyl alcohol, ethanol, isopropanol, citric acid, urea, cationized cellulose-fatty acid polypeptide condensate, lauric acid, pyrrolidone-carboxylate, and various types of amino acids may be exemplified. As a surfactant, nonionic surface active agents such as polyoxyethylene fatty acid partial ester, polyoxyethylene sorbitan fatty acid partial ester, polyoxyethylene glycerin fatty acid partial ester, polyglycerin fatty acid partial ester, fatty acid alkanol amide, fatty acid alkanol amide-ethylene oxide addition product, polyoxyethylene glycerin fatty acid, monoglycerin pyroglutaminate, glycerin acylglutaminate, etc.; anionic surface active agents such as alkyl sulfate, polyoxyethylene alkyl sulfate, fatty acid amide ether sulfate, alkylbenzene sulfate, alkyloxy sulfonate, sulfosuccinic acid higher alcohol ester salts, N-long-chain fatty acid acryl-N-methyl-taurine salts, fatty acid salts, N-long-chain acyl glutaminate, N-long-chain acyl sarcosine salts, monoalkyl phosphate, etc.; amphoteric surface active agents such as carboxybetaine type, imidazoline type, lecithin, aminosulfonic acid type, alkylamine oxide type, $N\alpha,N\alpha$-dimethyl or $N\alpha,N\alpha,N\alpha$-trimethyl-$N\epsilon$-acyl basic amino acids, etc.; and cationic surface active agents such as dialkyldimethylammonium chloride, alkyltrimathylammonium chloride, fatty acid acylalginine ethyl ester salts, etc may be exemplified. As a powder, inorganic powders such as talc, kaolin, titanium oxide, titanium-coated mica, mica, iron oxide, silicic ultramarine, prussian blue, zinc white, clay, precipitated calcium carbonate, etc.; and organic powders such as N-long-chain acyl basic amino acids, etc may be exemplified.

The cosmetic compositions of the present invention may further contain the usually used cosmetic adjuvants such as thickening agent, softener, wetting agent, superfatting agent, relaxing agent, preservative, defoaming agent, perfume, dye for coloring the composition itself or the skin, and other materials normally used in the cosmetics.

The cosmetic compositions of the present invention can be made into desired forms such as solution, emulsion, kneaded mixture, solid (pressed preparation), powder, etc., by properly selecting and adjusting the type and amount of the components compounded. As uses of the cosmetic compositions of the present invention, sun oil, lotion, cream, milky lotion, hair rinse, hair conditioner, liquid foundation, lipstick, foundation, face powder, aerosol, may be exemplified.

The content of the compounds of the formula (I) in the cosmetic compositions of the present invention may vary depending on the composition of the compounding ingredients and the sun protecting factors (SPF), but the content thereof is usually 0.1 to 20% by weight, preferably 0.5 to 10% by weight.

As the ultraviolet absorber to be contained in the cosmetic compositions of the present invention, one of the compounds represented by the general formula (I) may be used singly or not less than two these compounds may be used in combination. Also, at least one of the compounds of the general formula (I) may be used in combination with other types of ultraviolet absorber.

As the other types of ultraviolet absorbers that can be used in combination with the compound(s) of the general formula (I), camphor derivatives such as p-methylbenzylidene-D,L-camphor or sodium sulfonate thereof; benzophenones such as sodium 2-phenylbenzimidazole-5-sulfonate, sodium 3,4-dimethylphenylglyoxylate, isooctyl 4-phenylbenzophenone-2-carboxylate, etc.; and p-methoxycinnamic acid esters, 2-phenyl-5-methylbenzoxazole, 2-ethylhexyl salicylate, p-dimethylaminobenzoic acid esters and the like may be exemplified.

They can be used with an inorganic powder such as titanium oxide which serves as a scattering agent.

The compounds represented by the general formula (I) used in the present invention have a high molecular extinction coefficient of not less than $10^4$ at 270–320 nm. They also have a high absorptivity of ultraviolet rays of wavelength 290–320 nm which are believed to cause erythema of the skin and ultraviolet rays of wavelength 300–320 nm which are considered to cause deterioration of the resins such as polyethylene, polypropylene, polyvinyl chloride, etc. Also, the compounds of the general formula (I), owing to the effect of R, are markedly improved in solubility in various kinds of animal and vegetable oils, fats and oils, and organic solvents as compared with the known compounds, for example, N-benzoyl-α-dehydrotyrosine and O-methyl-N-benzoyl-α-dehydrotyrosine. Further, the compounds of the general formula (I) in which the hydrogen atoms of the amide are substituted with an acetyl group exhibit even better solubility in various kinds of animal and vegetable oils, fats and oils, and organic solvents.

Thus, the compounds of the general formula (I) can be well dissolved in various kinds of animal and vegetable oils, fats and oil, and other organic solvents, and can provide stable compositions when they are added in the cosmetic preparations such as cream, milky lotion, foundation, hair cream, anti-sunburn oil, etc. Also, when these compounds are added to the resins such as polyethylene, polypropylene, polystyrene, polyvinyl chloride, ABS resin, polycarbonate, etc., the compounds of the present invention have good compatibility with these resins. The α-dehydroamino acid derivatives of the general formula (IV) used in the present invention, as compared with the commercially available ultraviolet absorbers (e.g. benzophenones UV absorber, triazoles UV absorber and salicylic acids UV absorbers), have the following advantages. (1) Their suppressing effect against the action of ultraviolet rays is excellent especially in the presence of oxygen. (2) They have excellent heat and light stability and their effect keeps long. (3) They have 2 to 10 times as high UV molecular extinction coefficient as that of the commercially available UV absorbers. (4) Because of good compatibility with various polymer materials, they can be used as a plasticizer for fibers, resins, etc., and also as a yellowing inhibitor.

As described above, the compounds of the present invention have a very wide scope of use, the fields of their use including perfume and cosmetic industries, plastic industries, organic pharmaceutical industries, photographic industries, food industries and textile industries.

Particularly, since the compounds of the present invention have absorptivity of ultraviolet rays of wavelength 240-360 nm (maximum absorptivity wavelength: 300-340 nm), when they are used in cosmetics, there are provided the anti-sunburn and anti-erythema cosmetics having unequaled selective UV absorptivity. Also, when they are mixed in the polymers such as polyethylene, polypropylene, polyvinyl chloride, etc., the deterioration of the polymers due to ultraviolet rays is markedly reduced.

The compounds represented by the general formula (V), especially those of the formula (V) wherein $X^2$ is a hydroxyl or methoxyl group have high absorptivity of ultraviolet rays of long wavelength region (320-400 nm) and are also soluble in various kinds of animal and vegetable oils, fats and oil, and organic solvents.

The compounds represented by the formula (I) have high UV absorptivity and excellent light and heat stability and are also non-stimulant and non-injurious to the skin, hair, mucosae and other tissues of the human body, so that when these compounds are blended in a suitable amount (selected from within the range of 0.1 to 20% by weight according to the purpose of use) in various kinds of cosmetic preparations such as oil, lotion, cream, milky lotion, hair rinse, hair conditioner, liquid foundation, lipstick, foundation, face powder, aerosol, etc., these cosmetic preparations prove to be ones which have excellent ultraviolet absorptivity and are stable to light and heat.

The typical examples of the compound according to the present invention, and the maximum absorptivity wavelength (the UV wavelength at which the compounds show the maximum UV absorptivity) and other properties measured with the typical examples of the compounds according to the present invention are shown in Tables 1 and 2 as Example 1. The solubility of the compounds in the organic solvents is shown in Table 3 as Example 10, and the typical examples of formulations using the compounds of the present invention are shown as Examples 11 to 23. The present invention, however, is not limited by these examples.

TABLE 1-1

Example 1

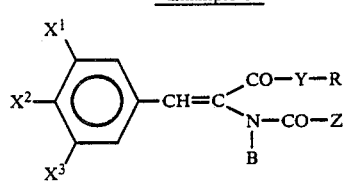
(IV)

| No. | Compound | $X^1$ | $X^2$ | $X^3$ | Y | B | Z | R |
|---|---|---|---|---|---|---|---|---|
| 1 | N-benzoyl-O-methyl-α-dehydrotyrosine isopropyl ester | H | OCH$_3$ | H | O | H | ⬡ | CH(CH$_3$)$_2$ |
| 2 | N-benzoyl-O-methyl-α-dehydrotyrosine 2-ethylhexyl ester | H | OCH$_3$ | H | O | H | ⬡ | CH$_2$CH(C$_4$H$_9$)(C$_2$H$_5$) |
| 3 | N-benzoyl-O-methyl-α-dehydrotyrosine n-lauryl ester | H | OCH$_3$ | H | O | H | ⬡ | C$_{12}$H$_{25}$ |

TABLE 1-1-continued

Example 1

$$\text{(IV)}$$

| No. | Compound | $X^1$ | $X^2$ | $X^3$ | Y | B | Z | R |
|---|---|---|---|---|---|---|---|---|
| 4 | N-benzoyl-O-methyl-α-dehydrotyrosine isostearyl ester | H | OCH$_3$ | H | O | H | phenyl | i-C$_{18}$H$_{37}$ |
| 5 | N-benzoyl-O-methyl-α-dehydrotyrosine cyclohexyl ester | H | OCH$_3$ | H | O | H | phenyl | cyclohexyl |
| 6 | N-benzoyl-O-methyl-α-dehydrotyrosine 3,3,5-trimethylcyclohexyl ester | H | OCH$_3$ | H | O | H | phenyl | 3,3,5-trimethylcyclohexyl |
| 7 | N-acetyl-N-benzoyl-O-methyl-α-dehydrotyrosine lauryl ester | H | OCH$_3$ | H | O | COCH$_3$ | phenyl | C$_{12}$H$_{25}$ |
| 8 | N-acetyl-O-methyl-α-dehydrotyrosine isopropyl ester | H | OCH$_3$ | H | O | H | CH$_3$ | CH(CH$_3$)$_2$ |
| 9 | N-acetyl-O-methyl-α-dehydrotyrosine n-lauryl | H | OCH$_3$ | H | O | H | CH$_3$ | C$_{12}$H$_{25}$ |
| 10 | N-benzoyl-O-methyl-α-dehydrotyrosine lauryl amide | H | OCH$_3$ | H | NH | H | phenyl | C$_{12}$H$_{25}$ |
| 20 | N-acetyl-N-benzoyl-O-methyl-α-dehydrotyrosine 2-ethylhexyl ester | H | OCH$_3$ | H | O | COCH$_3$ | phenyl | CH$_2$CH(C$_2$H$_5$)CH$_2$CH$_2$CH$_2$CH$_3$ |

TABLE 1-2

$$\text{(V)}$$

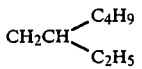

| No. | Compound | $X^1$ | $X^2$ | $X^3$ | W | R |
|---|---|---|---|---|---|---|
| 11 | N-butyl 4-benzylidene-2,5-dioxo-l-imidazolidinepropionate | H | H | H | H | n-C$_4$H$_9$ |
| 12 | Iso-butyl 4-benzylidene-2,5-dioxo-l-imidazolidinepropionate | H | H | H | H | i-C$_4$H$_9$ |
| 13 | 2-ethylhexyl 4-benzylidene-2,5-dioxo-l-imidazolidinepropionate | H | H | H | H | CH$_2$CH(C$_4$H$_9$)(C$_2$H$_5$) |
| 14 | Methyl 4-(3,4-dimethoxyphenylmethylene)- | OCH$_3$ | OCH$_3$ | H | H | CH$_3$ |

TABLE 1-2-continued $$\text{(V)}$$

Structure: X$^1$, X$^2$, X$^3$ substituted phenyl-CH=C(W-N)-C(=O)-N(CH$_2$CH$_2$CO-O-R)-C(=O) imidazolidine ring

| No. | Compound | X$^1$ | X$^2$ | X$^3$ | W | R |
|---|---|---|---|---|---|---|
| 15 | Ethyl 4-(3,4-dimethoxyphenylmethylene)-2,5-dioxo-l-imidazolidinepropionate | OCH$_3$ | OCH$_3$ | H | H | C$_2$H$_5$ |
| 16 | N-butyl 4-(3,4-dimethoxyphenylmethylene)-2,5-dioxo-l-imidazolidinepropionate | OCH$_3$ | OCH$_3$ | H | H | n-C$_4$H$_9$ |
| 17 | Iso-butyl 4-(3,4-dimethoxyphenylmethylene)-2,5-dioxo-l-imidazolidinepropionate | OCH$_3$ | OCH$_3$ | H | H | i-C$_4$H$_9$ |
| 18 | 2-ethylhexyl 4-(3,4-dimethoxyphenylmethylene)-2,5-dioxo-l-imidazolidinepropionate | OCH$_3$ | OCH$_3$ | H | H | CH$_2$CH(C$_4$H$_9$)(C$_2$H$_5$) |
| 19 | Diethyl 4-(3,4-dimethoxyphenylmethylene)-2,5-dioxo-1,3-imidazolidinedipropionate | OCH$_3$ | OCH$_3$ | H | CH$_2$CH$_2$CO—O—R | C$_2$H$_5$ |

TABLE 2-1, 2-2

Figure 2:
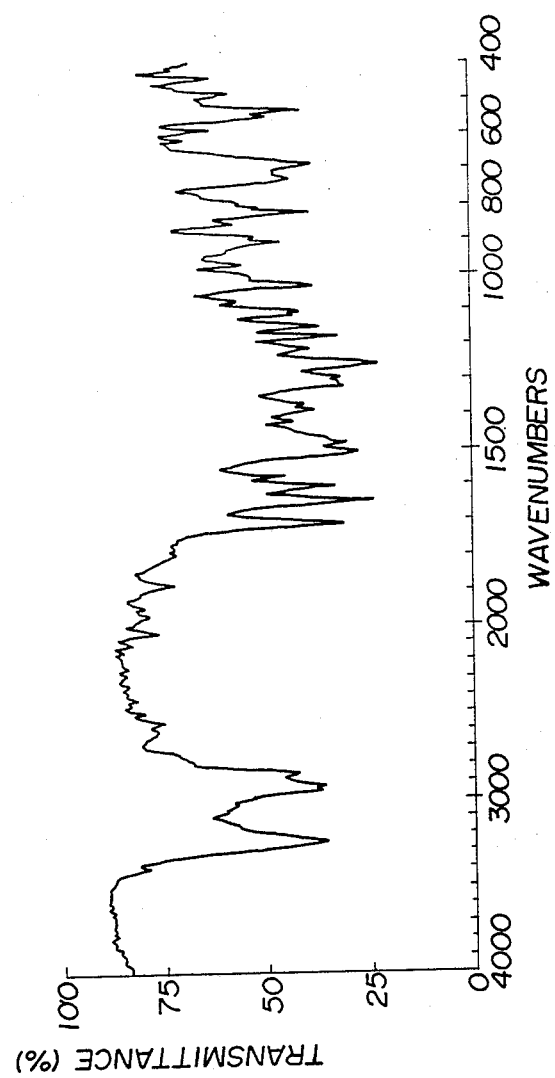
Figure 3:
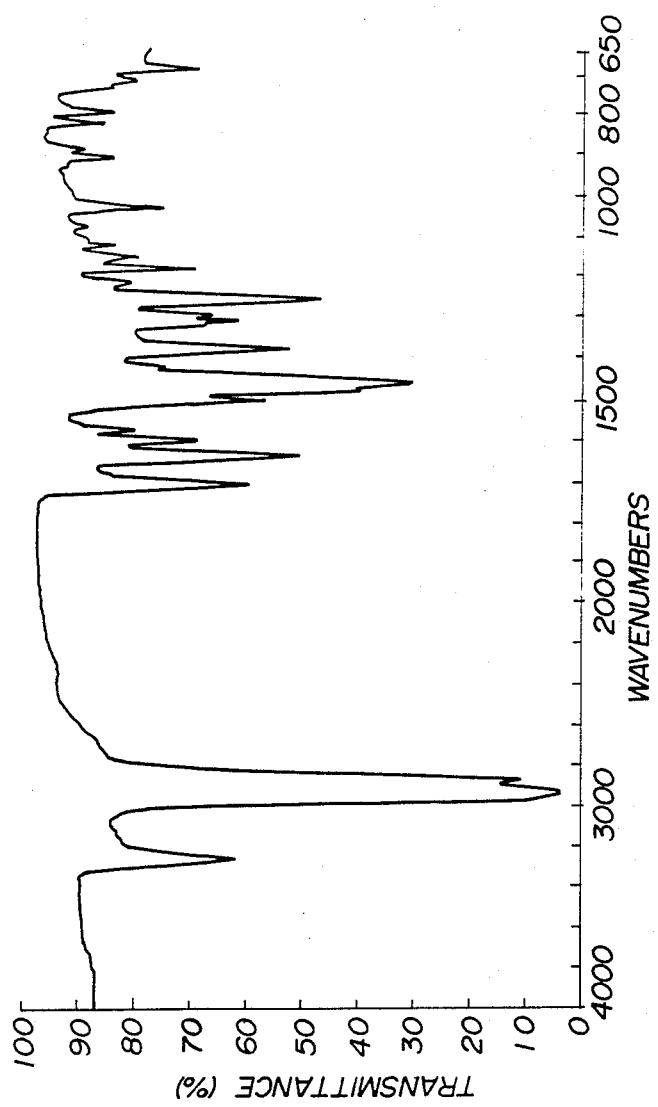
Figure 4:
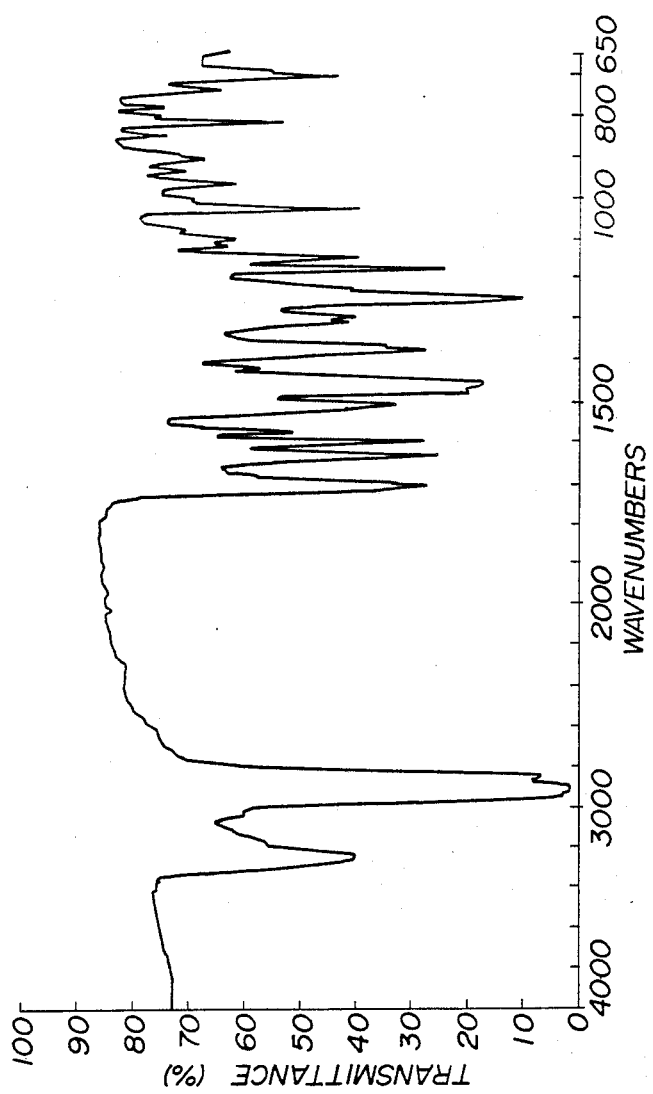
Figure 5:
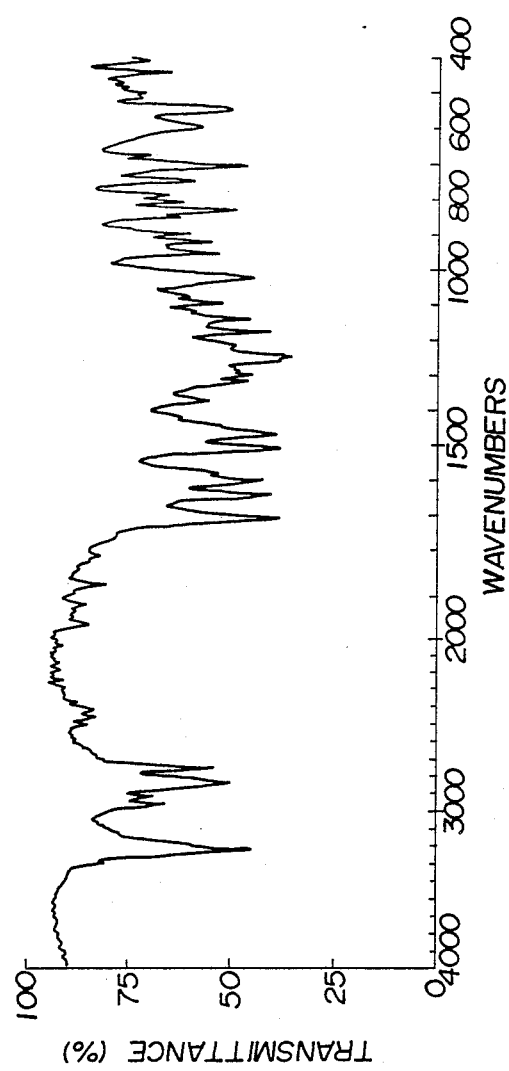
Figure 6:
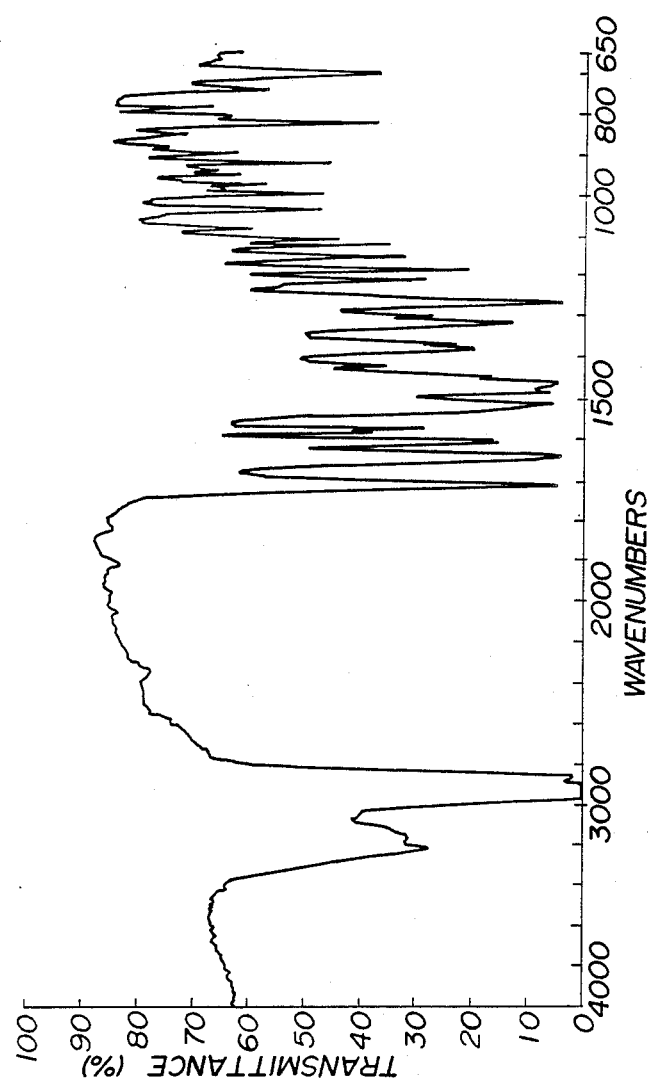
Figure 7:
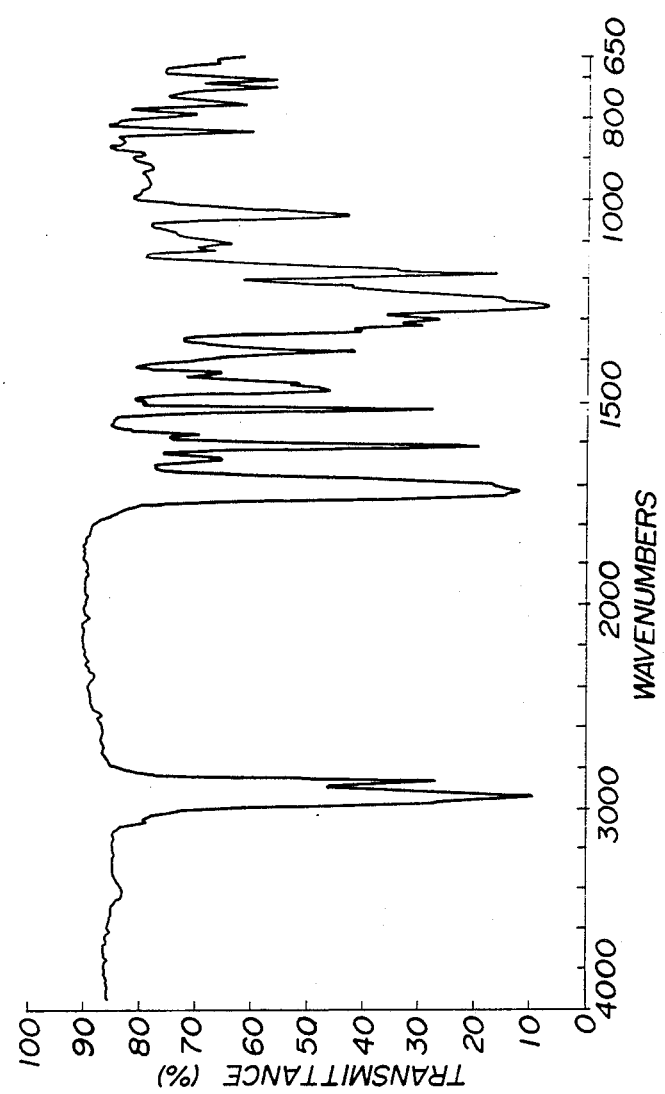
Figure 8:
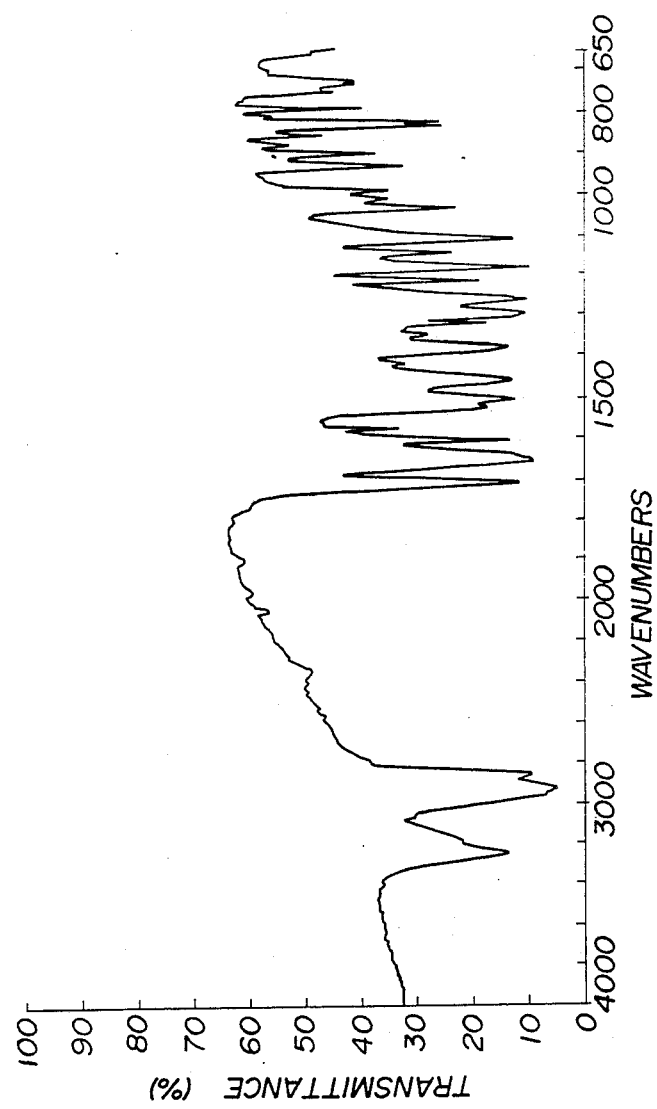
Figure 9:
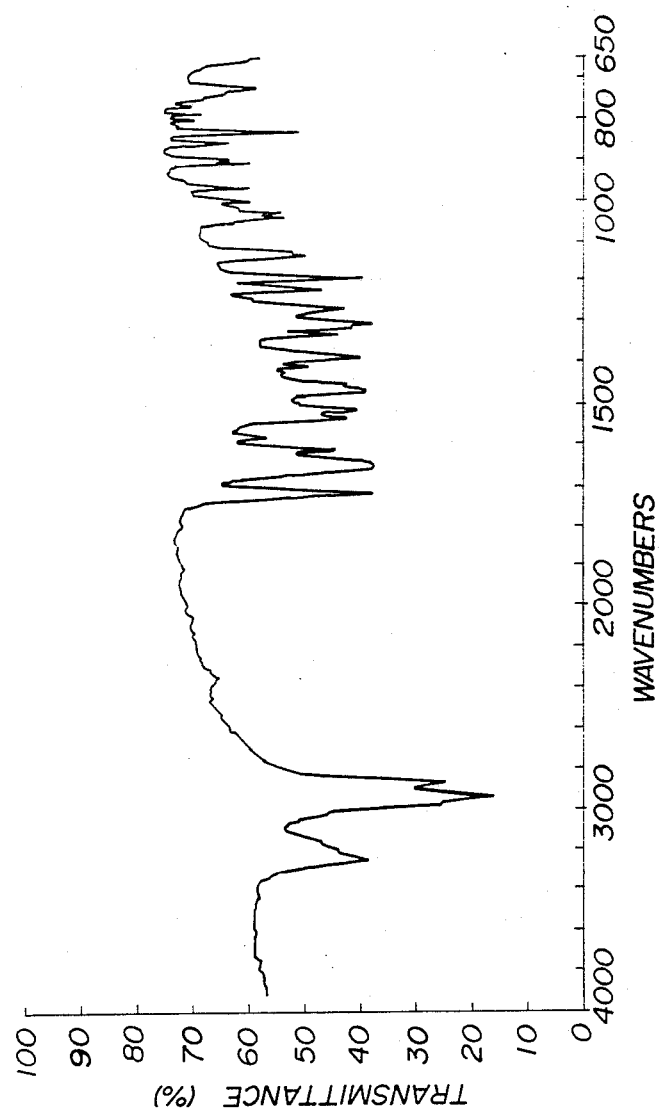
Figure 10:
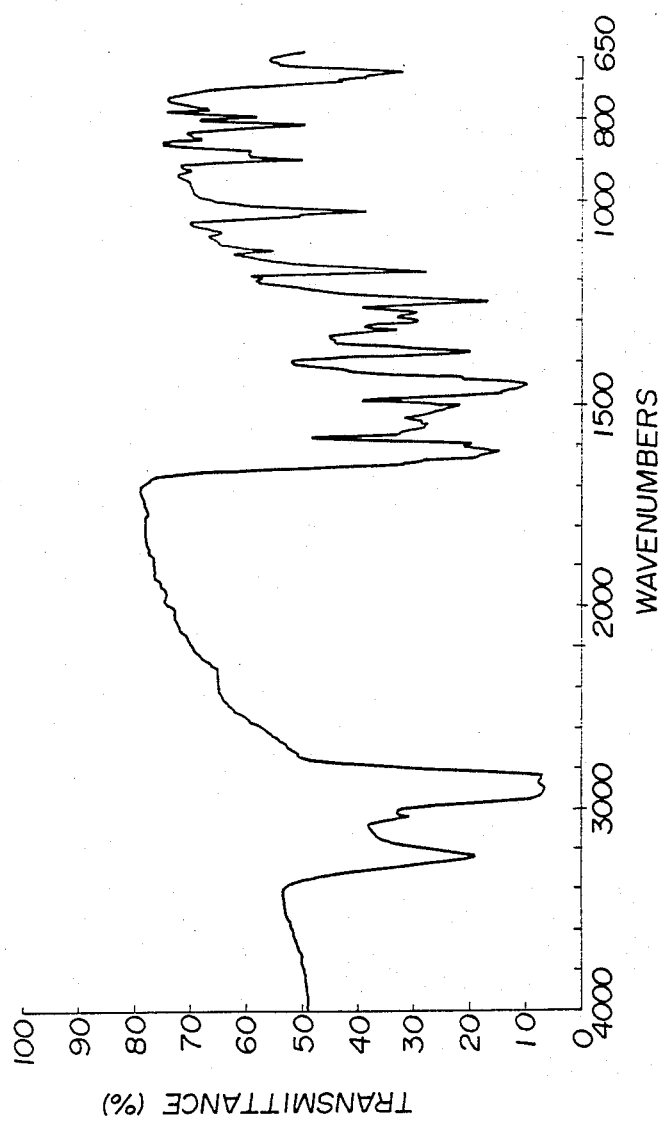
Figure 11:
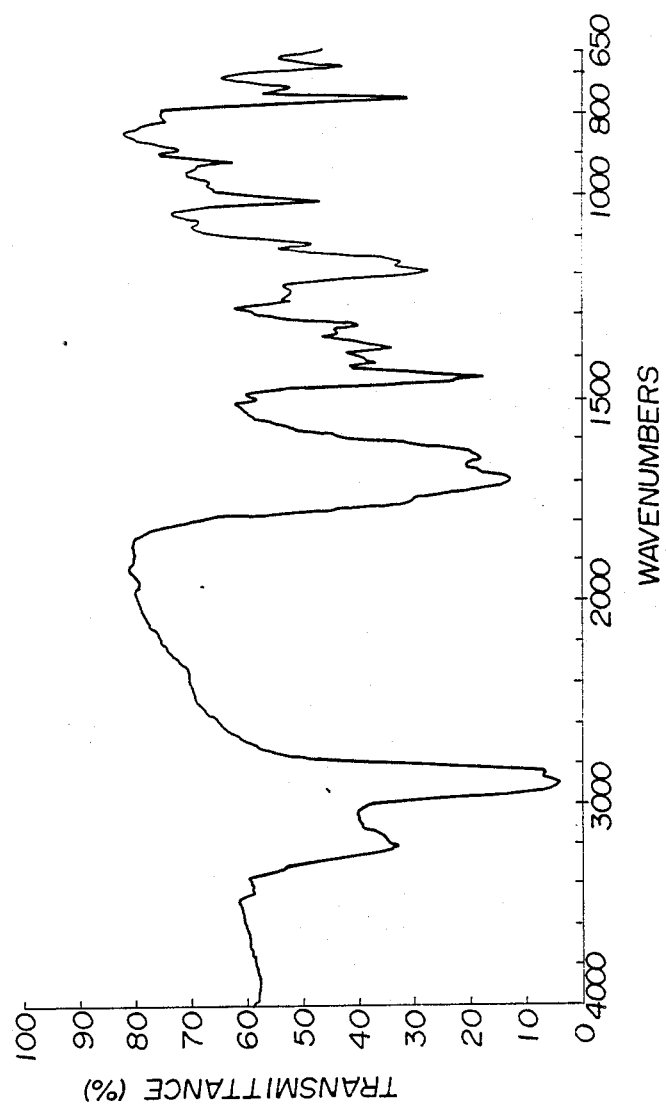
Figure 12:
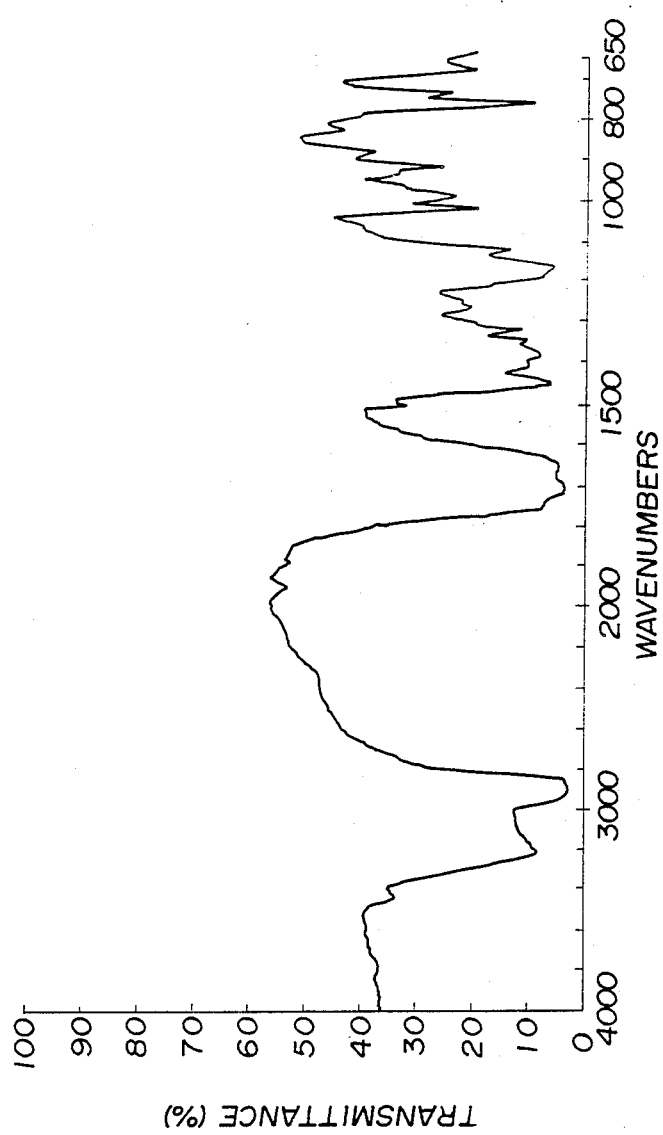
Figure 13:
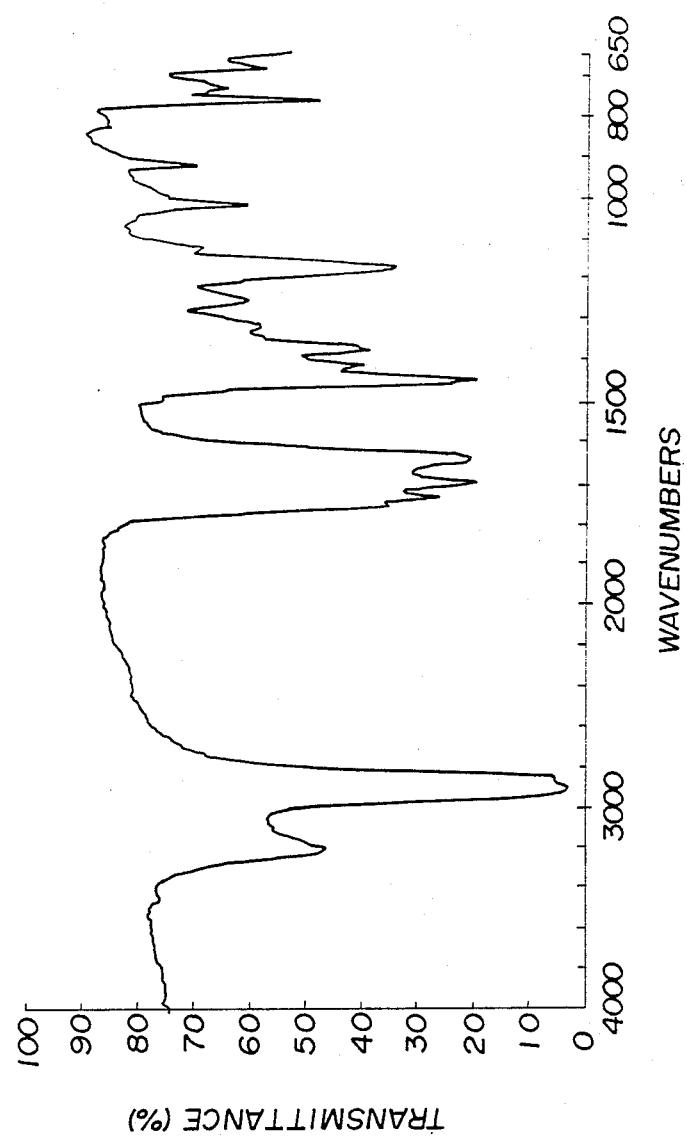
Figure 14:
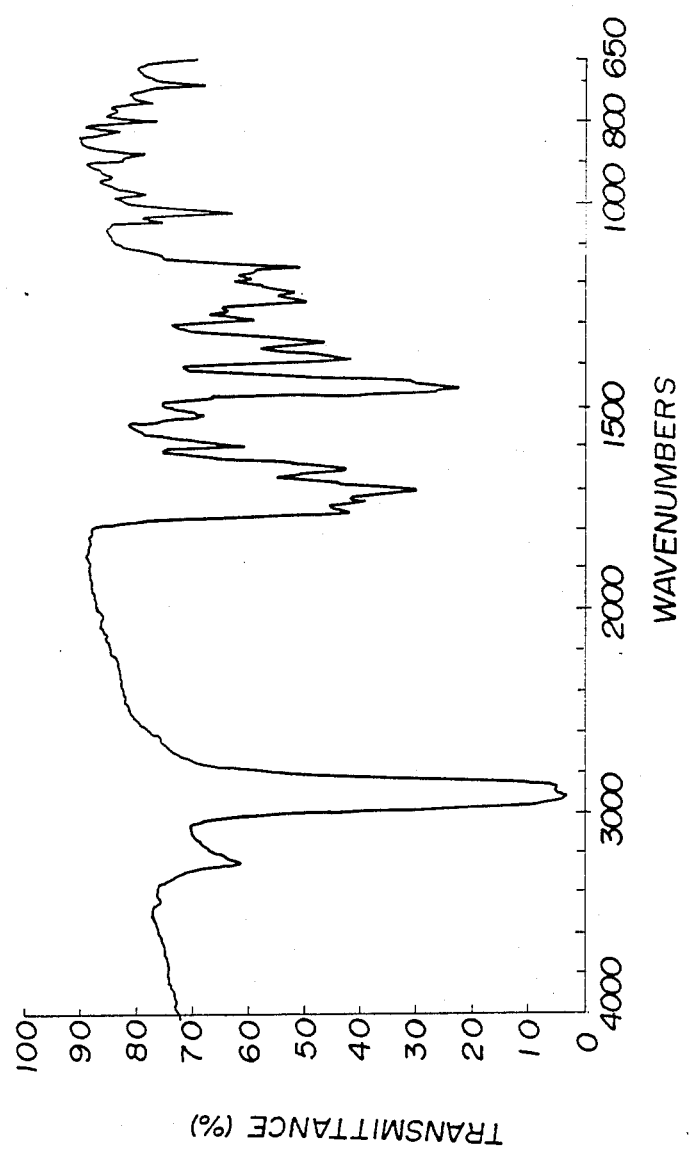
Figure 15:
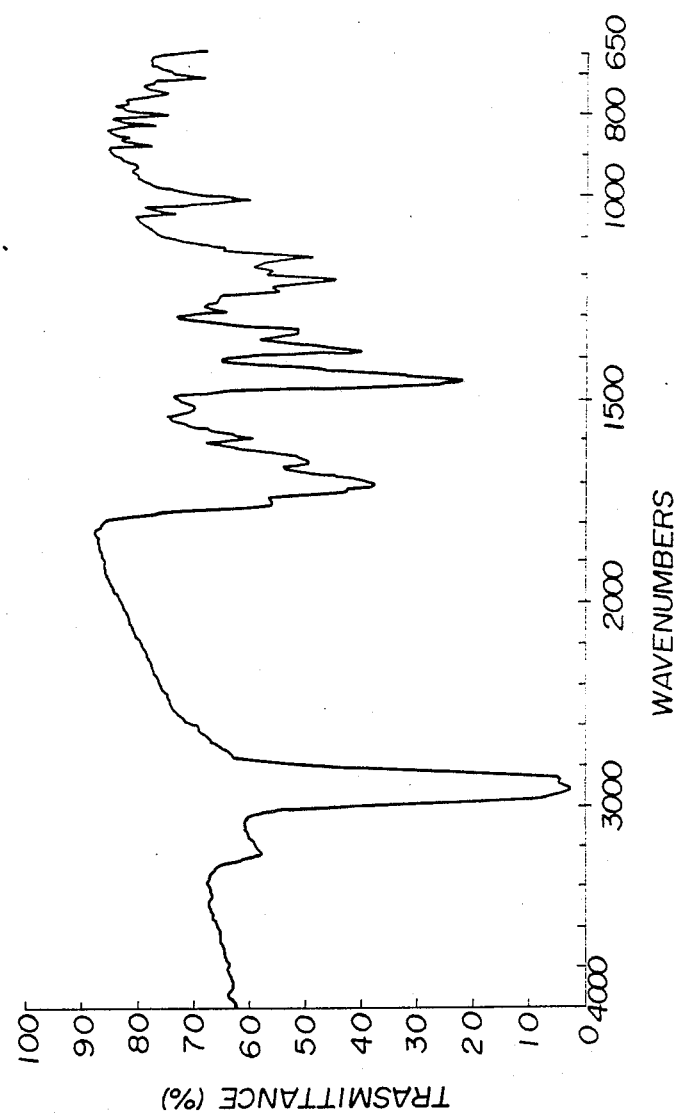

| No. | Compound | Melting point (°C.) | Mas. absorptivity wavelength (nm) | Molecular extinction coefficient | Mass spectrum (m/e) | Elemental analysis (%) | C | H | N | IP FIG. NO. |
|---|---|---|---|---|---|---|---|---|---|---|
| | Property values of α-dehydroamino acid derivatives represented by the formula (IV) | | | | | | | | | |
| 1 | N-benzoyl-O-methyl-α-dehydrotyrosine isopropyl ester | 141.5–144.5 | 309 309 | 22200 | 339 | Theoretical Found | 70.78 70.61 | 6.24 6.02 | 4.13 4.08 | FIG. 1 |
| 2 | N-benzoyl-O-methyl-α-dehydrotyrosine 2-ethylhexyl ester | 63.5–67.0 | 310 | 24900 | 409 | Theoretical Found | 73.32 73.52 | 7.63 7.44 | 3.42 3.51 | FIG. 2 |
| 3 | N-benzoyl-O-methyl-α-dehydrotyrosine n-lauryl ester | 102.0–111.5 | 310 | 19400 | 465 | Theoretical Found | 74.81 74.75 | 8.44 8.25 | 3.01 2.98 | FIG. 3 |
| 4 | N-benzoyl-O-methyl-α-dehydrotyrosine isostearyl ester | 123.0–126.5 | 310 | 21100 | 549 | Theoretical Found | 76.46 76.50 | 9.35 9.21 | 2.55 2.37 | FIG. 4 |
| 5 | N-benzoyl-O-methyl-α-dehydrotyrosine cyclohexyl ester | 127.0–129.0 | 310 | 23900 | 379 | Theoretical Found | 72.80 72.56 | 6.64 6.35 | 3.69 3.66 | FIG. 5 |
| 6 | N-benzoyl-O-methyl-α-dehydrotyrosine 3,3,5-trimethylcyclohexyl ester | 110.0–112.5 | 310 | 25100 | 421 | Theoretical Found | 72.35 72.40 | 9.58 9.29 | 3.25 3.08 | FIG. 6 |
| 7 | N-acetyl-N-benzoyl-O-methyl-α-dehydrotyrosine lauryl ester | * | 316 | 19800 | 507 | Theoretical Found | 73.34 73.62 | 81.4 8.04 | 2.76 2.92 | FIG. 7 |
| 8 | N-acetyl-O-methyl-α-dehydrotyrosine n-lauryl ester | 127.6–130.5 | 306 | 23900 | 277 | Theoretical Found | 64.97 64.99 | 6.91 6.87 | 5.05 5.12 | FIG. 8 |
| 9 | N-acetyl-O-methyl-α-dehydrotyrosine n-lauryl ester | 84.0–86.0 | 306 | 25500 | 403 | Theoretical Found | 71.43 71.65 | 9.24 9.03 | 3.47 3.55 | FIG. 9 |
| 10 | N-benzoyl-O-methyl-α-dehydrotyrosine lauryl amide | 102.0–111.5 | 302 | 22400 | 464 | Theoretical Found | 76.63 76.32 | 6.65 6.88 | 6.16 6.05 | FIG. 10 |
| | Property values of benzalhydantoin derivatives represented by the formula (V) | | | | | | | | | |
| 11 | N-butyl 4-benzylidene-2,5-dioxo-1-imidazolidinepropionate | 133.1–134.1 | 318 | 25280 (4.40) | 316 | Theoretical Found | 64.54 64.25 | 6.37 6.09 | 8.86 8.59 | FIG. 11 |
| 12 | Iso-butyl 4-benzylidene-2,5-dioxo-1-imidazolidinepropionate | 148.2–148.9 | 318 | 25280 (4.40) | 316 | Theoretical Found | 64.54 64.54 | 6.37 6.09 | 8.86 8.72 | FIG. 12 |
| 13 | 2-ethylhexyl 4-benzylidene-2,5-dioxo-1-imidazolidinepropionate | 102.5–103.2 | 317 | 26040 (4.40) | 372 | Theoretical Found | 67.72 57.49 | 7.58 7.29 | 7.52 7.37 | FIG. 13 |
| 14 | Methyl 4-(3,4-dimethoxyphenylmethylene)-2,5-dioxo-1-imidazolidinepropionate | 183.8 162.6 | 346 | 25300 (4.40) | 334 | Theoretical Found | 57.48 57.52 | 5.43 5.50 | 8.38 8.41 | FIG. 14 |
| 15 | Ethyl 4-(3,4-dimethoxy- | 161.5– | 346 | 24900 (4.40) | 348 | Theoretical | 58.61 | 5.79 | 8.04 | FIG. 15 |

TABLE 2-1, 2-2-continued

Figure 16:
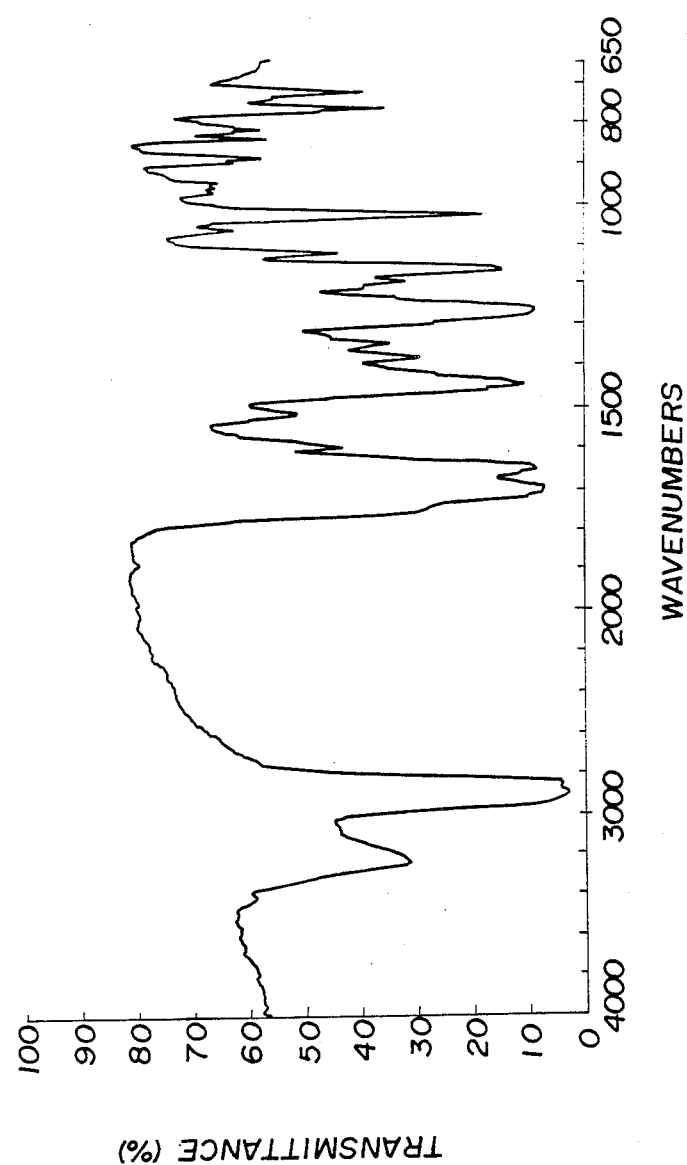
Figure 17:
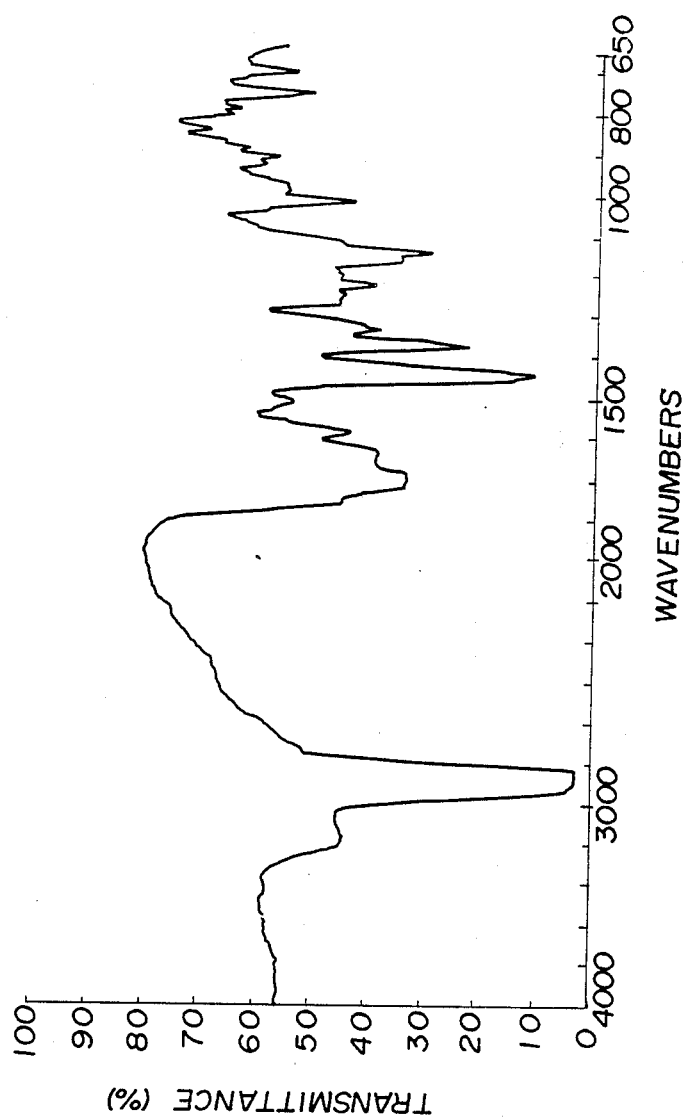
Figure 18:
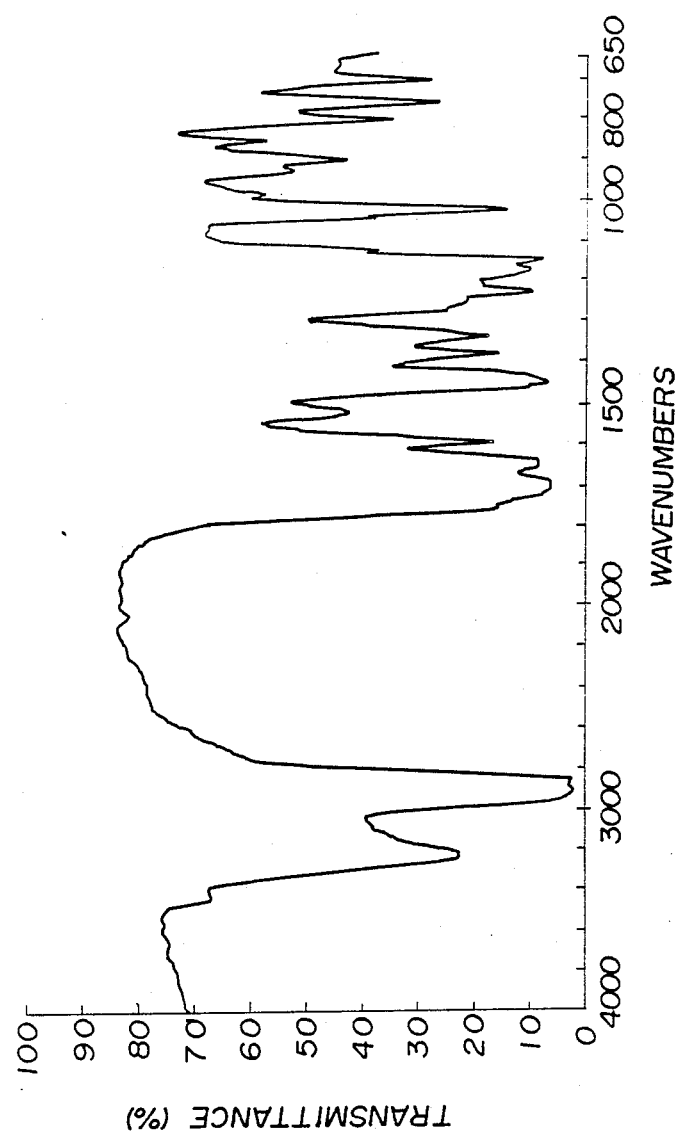
Figure 19:
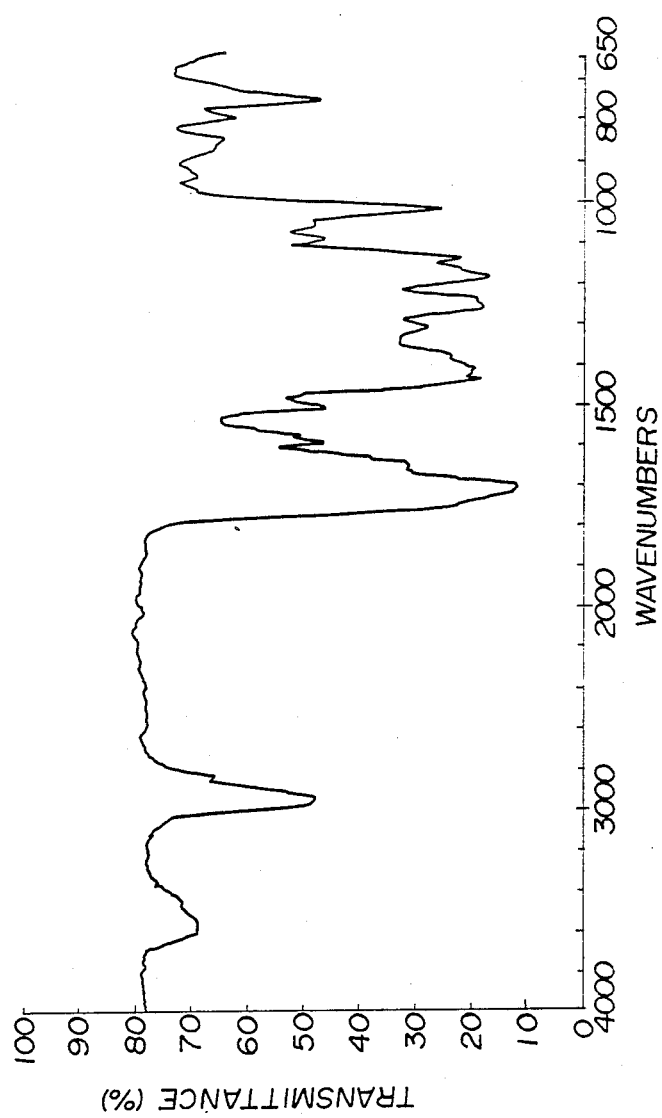

|  | | | | | | | | | | |
|---|---|---|---|---|---|---|---|---|---|---|
|  | phenylmethylene)2,5-dioxo-1-imidazolidinepropionate | 162.6 |  | (4.40) |  | Found | 55.35 | 5.95 | 7.98 | |
| 16 | N-butyl 4-(3,4-dimethoxyphenylmethylene)-2,5-dioxo-1-imidazolidinepropionate | 132.8–133.6 | 346 | 25200 (4.40) | 376 | Theoretical<br>Found | 60.63<br>60.58 | 6.43<br>6.66 | 7.44<br>7.18 | FIG. 16 |
| 17 | Iso-ethylhexyl 4-(3,4-dimethoxyphenylmethylene)-2,5-dioxo-1-imidazolidine-propionate | 146.5–147.3 | 346 | 24200 (4.38) | 376 | Theoretical<br>Found | 60.63<br>60.37 | 6.43<br>6.16 | 7.44<br>7.22 | FIG. 17 |
| 18 | 2-ethylhexyl 4-(3,4-dimethoxyphenylmethylene)-2,5-dioxo-1-imidazolidinepropionate | 102.2–103.2 | 348 | 22800 (4.36) | 432 | Theoretical<br>Found | 63.87<br>63.90 | 7.46<br>7.70 | 6.48<br>6.32 | FIG. 18 |
| 19 | Diethyl 4-(3,4-dimethoxyphenylmethylene)-2,5-dioxo-1,3-imidazolidine-dipropionate | oil | 334 | 14100 (4.15) | 448 | Theoretical<br>Found | 58.92<br>59.02 | 6.29<br>6.29 | 6.25<br>6.03 | FIG. 19 |

*Liquid

EXAMPLE 2

Synthesis Example 1

Synthesis of 2-phenyl-4-(4-methoxybenzylidene)-5-oxazolone 20 ml of anisaldehyde, 50 ml of acetic anhydride, 33.7 g of hippuric acid and 6.7 g of sodium acetate were mixed well and heated on a water bath for 30 minutes. The precipitated crystals were washed with hot water and then filtered. They were then recrystallized from benzene and dried to obtain 40 g of 2-phenyl-4-(4-methoxybenzylidene)-5-oxazolone. Yield: 83%.

Synthesis Example 2

Synthesis of N-benzoyl-O-methyl-α-dehydrotyrosine 2-ethylhexyl ester 1 kg of 2-phenyl-4-(4-methoxybenzylidene)-5-oxazolone obtained in Synthetsis Example 1 was suspended in 10 liters of toluene, and then 0.933 kg of 2-ethyl-1-hexanol and 0.029 kg of sodium hydroxide were added. The mixture was stirred at 25° C. for 4 hours, and then 40 liters of ethyl acetate and 40 liters of water were added, followed by further stirring of the mixture. The organic layer was separated, dried with Glauber's salt and concentrated under reduced pressure. The residue was recrystallized from toluene-hexane to obtain 1.0 kg of N-benzoyl-O-methyl-α-dehydrotyrosine 2-ethylhexyl ester (yield: 68.2%).

EXAMPLE 3

Synthesis of N-benzoyl-O-methyl-α-dehydrotyrosine n-lauryl ester 2 g of metallic sodium was added to 154 ml of n-lauryl alcohol and dissolved under heating. To this solution were added 118.6 g of 2-phenyl-4-(4-methoxyhenzylidene)-5-oxazolone obtained in Synthesis Example 1 and 300 ml of toluene, and the mixture was stirred at 25° C. for 8 hours. The resulting reaction solution was added with 2 liters of ethyl acetate, washed with 1.5 liters of 1N hydrochloric acid, 1.5 liters of 5% sodium hydrogencarbonate and 1.5 liters of water, then dried with Glauber's salt and concentrated under reduced pressure. The residue was recrystallized with n-hexane to obtain 163.5 g of N-benzoyl-O-methyl-α-dehydrotyrosine n-lauryl ester (yield: 82.7%).

EXAMPLE 4

Synthesis of N-acetyl-N-benzoyl-O-methyl-α-dehydrotyrosine n-lauryl ester 10 g of N-benzoyl-O-methyl-α-dehydrotyrosine n-lauryl ester obtained in Example 3 was dissolved in 100 ml of pyridine, followed by the addition of 20 ml of acetic anhydride and 0.5 g of dimethylaminopyridine, and the mixture was stirred at 25° C. for 14 hours. The reaction solution was concentrated under reduced pressure and the residue was dissolved in 300 ml of ethyl acetate. The solution was washed four times with 250 ml of water and again concentrated under reduced pressure. The residue was separated by silica gel column chromatography to obtain 8.8 g of N-acetyl-N-benzoyl-O-methyl-α-dehydrotyrosine n-lauryl ester (yield: 81.1%).

EXAMPLE 5

Synthesis of n-butyl 4-(3,4-dimethoxyphenylmethylene)-2,5-dioxo-1-imidazolidinepropionate 20 g (80.6 mmol) of 5-(3,4-dimethoxybenzylidine)-hydantoin, 12.4 g (96 mmol) of n-butyl acrylate and 0.90 g (1.6 mmol) of potassium hydroxide were added to 150 ml of dimethylformamide, and the mixture was stirred at 110° C. for 2 hours. The reaction solution was added with 200 ml of water and extracted with 500 ml of ethyl acetate. The extract was dried with sodium sulfate and then the solvent was distilled off under reduced pressure. Toluene was added to the residue and the precipitated crystals were dried to obtain 24.7 g of n-butyl 4-(3,4-dimethoxyphenylmethylene)-2,5-dioxo-1-imidazolidinepropionate (yield: 81.5 %).

EXAMPLE 6

Synthesis of 2-ethylhexyl 4-(3,4-dimethoxyphenylmethylene)-2,5-dioxo-1-imidazolidinepropionate 20 g (80.6 mmol) of 5-(3,4-dimethoxybenzylidene)-hydantoin, 17.8 g (96 mmol) of 2-ethylhexyl acrylate and 0.90 g (1.6 mmol) of potassium hydroxide were added to 150 ml of dimethylformamide, and the mixture was stirred at 110° C. for 2 hours. After cooling, the reaction solution was added with 200 ml of water and extracted with 500 ml of ethyl acetate. The extract was dried with sodium sulfate and then the solvent was distilled off under reduced pressure. The residue was recrystallized with toluene-n-hexane (1:1) and the precipitated crystals were dried to obtain 27.1 g of 2-ethylhexyl 4-(2,3-dimethoxyphenylmethylene)-2,5-dioxo-1-imidazolidinepropionate (yield: 77.8 %).

EXAMPLE 7 dried with sodium sulfate and concentrated under reduced pressure. The residue was dissolved in toluene and crystallized by adding hexane. The crystals were filtered out and dried to obtain 19.8 g of bis(2-ethylhexyl) 4-benzylidene-2,5-dioxo-1,3-imidazolidinedipropionate (yield: 42.3%).

TABLE 3

| | | (*1) Solubility of novel α-dehydroamino acid derivatives represented by the formula (IV) | | |
|---|---|---|---|---|
| No. | Compound | Ethanol (g/100 ml) | Olive oil (g/100 ml) | Liquid paraffin (g/100 ml) |
| (Control) | N-benzoyl-O-methyl-α-dehydrotyrosine | 0.7 | 0 | 0 |
| 1 | N-benzoyl-O-methyl-α-dehydro-tyrosine isopropyl ester | 8.0 | 0.3 | 0.4 |
| 2 | N-benzoyl-O-methyl-α-dehydro-tyrosine 2-ethyhexyl ester | >10.0 | >10.0 | 5.0 |
| 3 | N-benzoyl-O-methyl-α-dehydro-tyrosine n-lauryl ester | >10.0 | 3.7 | 1.0 |
| 4 | N-benzoyl-O-methyl-α-dehydro-tyrosine isostearyl ester | 5.0 | 1.3 | 0.5 |
| 5 | N-benzoyl-O-methyl-α-dehydrotyrosine 3,3,5-trimethylcyclohexylester | >10.0 | 3.0 | 1.0 |
| 6 | N-benzoyl-O-methyl-α-dehydrotyrosine 3,3,5-trimethylcyclohexyl ester | 10.0 | 3.0 | 1.0 |
| 7 | N-acetyl-N-benzoyl-O-methyl-α-dehydrotyrosine lauryl ester | >10.0 | >10.0 | 4.0 |
| 8 | N-acetyl-O-methyl-α-dehydro-tyrosine isopropropyl ester | >10.0 | 1.0 | 1.0 |
| 9 | N-acetyl-O-methyl-α-dehydro-tyrosine n-lauryl ester | 8.0 | 1.0 | 1.0 |

(*1) Grams of the sample dissolved in 100 ml of the solvent.

Synthesis of diethyl 4-(3,4-dimethoxyphenylmethylene)-2,5-dioxo-1,3-imidazolidinedipropionate 20 g (80.6 mmol) of 5-(3,4-dimethoxybenzylidene)-hydantoin, 17.7 g (177 mmol) of ethyl acrylate and 0.90 g (1.6 mmol) of potassium hydroxide were added to 150 ml of dimethylformamide (DMF), and the mixture was stirred at 110° C. for 2 hours. After cooling, the reaction solution was added with 200 ml of water and extracted with 500 ml of ethyl acetate. The extract was dried with sodium sulfate and the solvent was distilled off under reduced pressure. The residue was separated and purified by silica gel column chromatography [eluent: toluene/ethyl acetate (3/1)] to obtain 22.5 g of diethyl 4-(3,4-dimethoxyphenylmethylene)-2,5-dioxo-1,3-imidazolidinedipropionate (yield: 62.3%).

EXAMPLE 8

Synthesis of isobutyl 4-benzylidene-2,5-dioxo-1-imidazolidine-propionate 20 g (0.106 mol) of benzalhydantoin, 14.9 g (0.117 mol) of isobutyl acrylate and 1.2 g (0.02 mol) of potassium hydroxide were added to 150 ml of DMF, and the mixture was stirred at 110° C. for 2 hours. After cooling, the reaction solution was added with 300 ml of toluene and crystallized. The crystals were filtered out and dried to obtain 27.2 g of isobutyl 4-benzylidene-2,5-dioxo-1-imidazolidinepropionate (yield: 81%).

EXAMPLE 9

Synthesis of bis(2-ethylhexyl) 4-benzylidene-2,5-dioxo-1,3-imidazolidinedipropionate 10 g (53.1 mmol) of benzalhydantoin, 23.6 g (127.6 mmol) of 2-ethylhexyl acrylate and 0.6 g (10.6 mmol) of potassium hydroxide were added to 100 ml of DMF, and the mixture was stirred at 110° C. for 2 hours. After cooling, the reaction solution was extracted with ethyl acetate, and the organic layer was washed with water,

EXAMPLE 11: Sun oil

The materials shown below were compounded in the shown amounts to prepare a sun oil. The more advantageous conditions for homogenizing the following composition are to mix the materials while heating at about 40° to 45° C.

| | |
|---|---|
| N-benzoyl-O-methyl-α-dehydrotyrosine iso-stearyl ester (compound No. 4) | 4% by weight |
| Cacao oil | 2.5% by weight |
| Perfume | 0.5% by weight |
| Fatty acid triglyceride ($C_8$–$C_{12}$) | 93% by weight |

EXAMPLE 12: Skin protective cream (O/W type)

Components of (A) and (B) were respectively dissolved under heating according to the following formulations, and they were mixed and cooled to room temperature to prepare a skin protective cream.

| | |
|---|---|
| (A) | |
| Diethyl 4-(3,4-dimethoxyphenyl)methylene-2,5-dioxo-1,3-imidazolidinedipropionate (compound No. 19) | 8% by weight |
| N-benzoyl-O-methyl-α-dehydrotyrosine 3,3,5-trimethyl cycylhexyl ester (compound No. 19) | 8% by weight |
| Fatty acid triglyceride ($C_8$–$C_{12}$) | 10% by weight |
| Cetyl alcohol | 1.5% by weight |
| Polyoxyethylene cetyl ether and polyoxyethylene stearyl ether (10 E.O.) | 6% by weight |
| Polyoxyethylene sorbitan monostearate (20 E.O.) | 2% by weight |
| (B) | |
| Glycerin | 1.5% by weight |
| Propylene glycol | 1.5% by weiqht |
| Sorbitol solution (70%) | 3.5% by weight |

| -continued | |
|---|---|
| Sodium pyrrolidonecarboxylate | 0.5% by weight |
| Methyl para-oxybenzoate | 0.2% by weight |
| Water | 57% by weight |

EXAMPLE 13: Skin protective cream (W/O type)

The following components were compounded and treated in the same way as Example 12 to prepare a skin protective cream.

| (A) | |
|---|---|
| N-benzoyl-O-methyl-α-dehydrotyrosine 2-ethylhexyl ester (compound No. 2) | 8% by weight |
| Cetyl alcohol | 1.5% by weight |
| Beeswax | 1.5% by weight |
| Paraffin oil | 3% by weight |
| Cholesterol | 1% by weight |
| Fatty acid triglyceride ($C_8$–$C_{12}$) | 8% by weight |
| Glycerin monostearate | 5% by weight |
| Sorbitan monopalmitate | 9% by weight |
| Polyoxyethylene sorbitan monostearate (20 E.O.) | 1% by weight |
| Ceresine | 5% by weight |
| Whale wax | 2% by weight |
| Propyl para-oxybenzoate | 0.1% by weight |
| (B) | |
| Glycerin | 1.5% by weight |
| Propylene glycol | 1.5% by weight |
| Sorbitol solution (70%) | 4% by weight |
| Methyl para-oxybenzoate | 0.2% by weight |
| Water | 47.7% by weight |

EXAMPLE 14: Sun milk (milky lotion)

The following components were compounded and treated in the same way as Example 12 to prepare a sun milk.

| (A) | |
|---|---|
| 2-ethylhexyl 4-benzylidene-2,5-dioxo-1-imidazolidinedipropionate (compound No. 13) | 5% by weight |
| 2-ethylhexyl 4-(3,4-dimethoxyphenyl)methylene-2,5-dioxo-1-imidazolidinepropionate (compound No. 18) | 2% by weight |
| Polyoxyethylene cetyl ether and stearyl ether (10 E.O.) | 5% by weight |
| Vaseline oil | 6% by weight |
| Isopropyl myristate | 3% by weight |
| Silicone oil | 1% by weight |
| Cetyl alcohol | 1% by weight |
| Antiseptic | proper amount |
| Perfume | proper amount |
| Water | balance |

EXAMPLE 15: Sun milk (milky lotion)

The following components ere compounded and treated in the same way as Example 12 to prepare a sun milk.

| (A) | |
|---|---|
| Isobutyl 4-benzylidene-2,5-dioxo-1-imidazolidinedipropionate (compound No. 12) | 5% by weight |
| Liquid paraffin | 22.6% by weight |
| Solid paraffin | 4.5% by weight |
| Cetanol | 4% by weight |
| Sorbitan monostearate | 1.8% by weight |
| Polyoxyethylene sorbitan monostearate (20 E.O.) | 2.8% by weight |
| $N_\delta$-cocoyl ornithin | 5% by weight |
| (B) | |
| Triethanolamine pyrrolidone-carboxylate | 4% by weight |
| Water | 50.1% by weight |
| Antiseptic | 0.2% by weight |

EXAMPLE 16: Anti-sunburn lotion

The components (A) were dissolved under heating according to the following formulation and cooled to room temperature, and then the component (B) was added thereon to prepare an anti-su burn lotion.

| (A) | |
|---|---|
| N-benzoyl-O-methyl-α-dehydrotyrosine cyclohexyl ester (compound No. 5) | 2% by weight |
| Glycerin | 5% by weight |
| Polyethylene glycol 400 | 0.5% by weight |
| Perfume | proper amount |
| Water | balance |
| (B) | |
| 96% ethanol | 40% by weight |

EXAMPLE 17: Lipstick

A lipstick was prepared according to the following formulation. A part of (B) was added to (A) and the mixture was subjected to rolling to prepare the pigment portion. Then the components of (B) dissolved by heating were added thereto and the mixture was homogenized, rapidly cooled for solidifying it, and then shaped.

| (A) | |
|---|---|
| Titanium dioxide | 2% by weight |
| N-benzoyl-O-methyl-α-dehydrotyrosine isopropyl ester (compound No.1) | 5.7% by weight |
| (B) | |
| Hexadecyl alcohol | 25% by weight |
| Lanolin | 4% by weight |
| Beeswax | 5% by weight |
| Ozocerite | 4% by weight |
| Candelilla wax | 7% by weight |
| Carnauba wax | 2% by weight |
| Antioxidant | proper amount |
| Perfume | proper amount |
| Castor oil | balance |

EXAMPLE 18: Oily sun gel

The fatty materials were dissolved b heating to 40°–45° C. according to the following formulation, then silica was added thereto under stirring, and the mixture was cooled to prepare an oily sun gel.

| | |
|---|---|
| N-benzoyl-O-methyl-α-dehydrotyrosine lauryl ester (compound No.3) | 3% by weight |
| 2-ethylhexyl p-methoxycinnamate | 2% by weight |
| Cacao fat | 2.5% by weight |
| Silica | 10% by weight |
| Antioxidant | proper amount |
| Perfume | proper amount |
| Fatty acid triglyceride ($C_8$–$C_{12}$) | balance |

EXAMPLE 19: Effervescent air spray 90 parts of a mixture of the following composition and 10 parts of Freon gas (F21/F114=40/60) were charged into a pressure vessel to make an effervescent air spray.

| | |
|---|---|
| N-acetyl-N-benzoyl-O-methyl-α-dehydrotyrosine lauryl ester (compound No.7) | 0.3% by weight |
| Stearic acid | 7% by weight |
| Propylene glycol | 7% by weight |
| Triethanolamine | 6% by weight |
| Olive oil | 2% by weight |
| Water | balance |

EXAMPLE 20: No-effervescent lotion air spray 30 parts of a mixture of the following composition and 70 parts of Freon gas (F21/F114=40/60) were charged into a pressure vessel to make a non-effervescent lotion air spray.

| | |
|---|---|
| N-acetyl-O-methyl-α-dehydrotyrosine isopropyl ester (compound No.8) | 1% by weight |
| Propylene glycol | 10% by weight |
| 99% ethanol | 30% by weight |
| Water | balance |

EXAMPLE 21: Foundation

The components (C) were mixed and dissolved by heating at 70° C. according to the following formulation (oil phase). Separately, the components (B) were mixed and dissolved and maintained at 70° C. (aqueous phase). The components (A) were dispersed in the aqueous phase, to which the oil phase was added and emulsified, and then the mixture was cooled to prepare a foundation.

| | |
|---|---|
| (A) | |
| N-butyl 4-benzylidene-2,5-dioxo-1-imidazolidinepropionate (compound No. 11) | 10% by weight |
| Titanium oxide | 6% by weight |
| Red iron oxide | 1.5% by weight |
| Yellow iron oxide | 0.2% by weight |
| (B) | |
| Monomagnesium N-lauroylglutaminate | 0.5% by weight |
| Triethanolamine | 1.4% by weight |
| Propylene glycol | 9.5% by weight |
| Water | 37.9% by weight |
| (C) | |
| Stearic acid | 2.8% by weight |
| Propylene glycol monostearate | 2.8% by weight |
| Glycerin monosterarate (Self-emulsifiable type) | 2.8% by weight |
| Liquid paraffin | 24.6% by weight |

EXAMPLE 22: Face powder

The materials were mixed according to the following formulation to obtain a face powder.

| | |
|---|---|
| N-benzoyl-O-methyl-α-dehydrotyrosine lauryl amide (compound No. 10) | 72.4% by weight |
| Talc | 10% by weight |
| Titanium oxide | 1% by weight |
| Kaolin | 5% by weight |
| Nε-lauroyllysine | 5% by weight |
| Zinc laurate | 1.8% by weight |
| Iron oxide (red, yellow and black) | 1.8% by weight |
| Perfume | 3% by weight |

EXAMPLE 23: Rinse

The components (A) were mixed and dissolved by heating at 80° C. according to the following formulation, and then (B) was added and dispersed therein. To this dispersion was added (C) which had been dissolved at 80° C., and the solution was mixed and emulsified and then cooled to room temperature

| | |
|---|---|
| (A) | |
| N-acetyl-O-methyl-α-dehydrotyrosine isopropyl ester (Compound No. 8) | 1% by weight |
| Cation DS (note 1) | 1% by weight |
| CAE (note 2) | 0.5% by weight |
| Polyoxyethylene sorbital monooleate (4 E.O.) | 0.5% by weight |
| Polyoxyethylene sorbital monooleate (25 E.O.) | 0.5% by weight |
| Water | 80.5% by weight |
| (B) | |
| Nε-lauroyllysine | 2% by weight |
| (C) | |
| Liquid paraffin | 2% by weight |
| Cetanol | 3% by weight |

What is claimed is:

1. An ultraviolet absorber composition comprising an inert carrier and an effective amount of at least one compound of the formula (I)

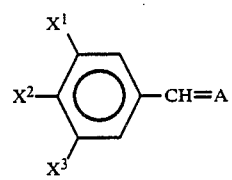

(I)

wherein A represents

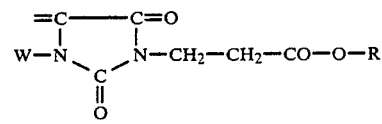

wherein:
W is a hydrogen atom or a group —CH$_2$—CH$_2$—CO—O—R;
X$^1$, X$^2$ and X$^3$ each represents independently a hydrogen atom, a hydroxyl group or a methoxy group, wherein two or three of X$^1$, X$^2$ and X$^3$ are the same of all are different; and
R is a straight chain alkyl group having 1 to 18 carbon atoms, or a branched or a cyclic alkyl group having 3 to 18 carbon atoms,
provided that when X$^1$, X$^2$ an X$^3$ are a hydrogen atom, R is a straight chain, a branched or a cyclic alkyl group having 3 to 18 carbon atoms.

2. The ultraviolet absorber composition of claim 1, wherein X$^1$ and X$^3$ are a hydrogen atom of a methoxyl group, X$^2$ is a methoxyl group or a hydroxyl group, W is a hydrogen atom or a group —CH$_2$—CH$_2$—COOR, and R is a straight chain alkyl group having 1 to 18 carbon atoms, or a branched or a cyclic alkyl group having 3 to 18 carbon atoms.

3. The ultraviolet absorber composition of claim 1, wherein X$^1$, X$^2$ and X$^3$ are a hydrogen atom, W is a hydrogen atom or a group —CH$_2$—C$_2$—COOR, and R is a straight chain, a branched or a cyclic alkyl group having 3 to 18 carbon atoms.

4. The ultraviolet absorber composition according to claim 1, wherein A is

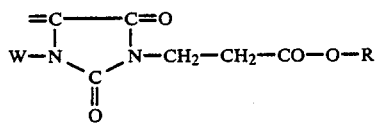

$X^1$ and $X^3$ are hydrogen atom or a methoxyl group, $X^2$ is a methoxyl group or a hydroxyl group, W is hydrogen atom or $-CH_2-CH_2-COOR$, and R is a straight chain alkyl group having 1 to 18 carbon atoms, or branched or cyclic alkyl group having 3 to 18 carbon atoms.

5. The ultraviolet absorber composition according to claim 1, wherein A is

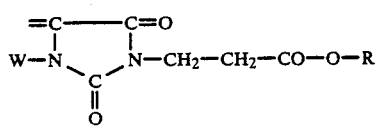

$X^1$, $X^2$ and $X^3$ are hydrogen atom, W is hydrogen atom or $-CH_2-CH_2-COOR$, and R is a straight chain, branched or cyclic alkyl group having 3 to 18 carbon atoms.

6. The ultraviolet absorber composition according to claim 4, wherein $X^1$ and $X^2$ are a methoxyl group, $X^3$ is hydrogen atom, W is hydrogen atom or $-CH_2-CH_2-CO-O-R$ and R is a methyl group, an ethyl group, an isopropyl group, an n-butyl group, an isobutyl group, an amyl group, an isoamyl group, an n-hexyl group, a cyclohexyl group, an n-octyl group, a 2-ethylhexyl group, a 2,2,4-trimethylcyclohexyl group, a decyl group, a lauryl group, a myristyl group, a cetyl group or a stearyl group.

7. The ultraviolet absorber composition according to claim 5, wherein $X^1$, $X^2$ and $X^3$ are hydrogen atom, W is hydrogen atom or $-CH_2-CH_2-CO-O-R$ and R is an isopropyl group, an n-butyl group, an isobutyl group, an amyl group, an isoamyl group, an n-hexyl group, a cyclohexyl group, an n-octyl group, a 2-ethylhexyl group, a 2,2,4-trimethylcyclohexyl group, a decyl group, a lauryl group, a myristyl group, a cetyl group or a stearyl group.

8. The ultraviolet absorber composition according to claim 1, wherein B is hydrogen atom or an acetyl group, $X^1$ and $X^3$ are hydrogen atom, $X^2$ is a methoxyl group, Y is oxygen atom or an imino group ($-NH-$), Z is a methyl or phenyl group, and R is an isopropyl, 2-ethylhexyl, lauryl, isostearly, cyclohexyl or 3,3,5-trimethylcyclohexyl group.

9. The ultraviolet absorber composition according to claim 6, wherein $X^1$ and $X^2$ are a methoxyl group, $X^3$ is hydrogen atom, W is hydrogen atom or $-CH_2CH_2COOR$, and R is a methyl, ethyl, n-butyl, isobutyl or 2-ethylhexyl group.

10. The ultraviolet absorber composition according to claim 7, wherein $X^1$, $X^2$ and $X^3$ are hydrogen atom, W is hydrogen atom, and R is an n-butyl, isobutyl or 2-ethylhexyl group.

* * * * *